(12) United States Patent
Bertoletti et al.

(10) Patent No.: US 9,334,317 B2
(45) Date of Patent: May 10, 2016

(54) HEPATITIS B VIRUS SPECIFIC ANTIBODY AND USES THEREOF

(75) Inventors: Antonio Bertoletti, Singapore (SG); Sastry Konduru Seetharama, Singapore (SG); Paul Anthony Macary, Singapore (SG); Soh Ha Chan, Singapore (SG); Chien Tei Too, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 290 days.

(21) Appl. No.: 13/511,116

(22) PCT Filed: Nov. 19, 2010

(86) PCT No.: PCT/SG2010/000440
§ 371 (c)(1),
(2), (4) Date: May 21, 2012

(87) PCT Pub. No.: WO2011/062562
PCT Pub. Date: May 26, 2011

(65) Prior Publication Data
US 2012/0308580 A1    Dec. 6, 2012

Related U.S. Application Data

(60) Provisional application No. 61/262,906, filed on Nov. 19, 2009.

(30) Foreign Application Priority Data

Jun. 21, 2010 (SG) .................. 201004457-6

(51) Int. Cl.
| | | |
|---|---|---|
| C07K 16/10 | (2006.01) |
| C12N 15/06 | (2006.01) |
| C07H 21/04 | (2006.01) |
| A61K 39/42 | (2006.01) |
| C07K 16/08 | (2006.01) |
| G01N 33/574 | (2006.01) |
| G01N 33/576 | (2006.01) |

(52) U.S. Cl.
CPC ............ *C07K 16/082* (2013.01); *G01N 33/574* (2013.01); *G01N 33/5761* (2013.01); *G01N 33/57407* (2013.01); *C07K 2317/32* (2013.01); *C07K 2317/90* (2013.01); *G01N 2333/02* (2013.01); *G01N 2800/52* (2013.01)

(58) Field of Classification Search
CPC ....... A61K 39/20; C07K 14/00; C12N 273/00
See application file for complete search history.

(56) References Cited

U.S. PATENT DOCUMENTS

| | | | |
|---|---|---|---|
| 5,972,656 A | 10/1999 | Lopez et al. | |
| 6,992,176 B2 * | 1/2006 | Reiter et al. | 530/388.22 |
| 2005/0255101 A1 | 11/2005 | Reiter et al. | |
| 2009/0232839 A1 | 9/2009 | Figdor et al. | |
| 2011/0318369 A1 * | 12/2011 | Reiter et al. | 424/174.1 |

FOREIGN PATENT DOCUMENTS

| | | |
|---|---|---|
| WO | 94/26784 A1 | 11/1994 |
| WO | 01/81421 A1 | 11/2001 |
| WO | 2007/027714 | 3/2007 |

OTHER PUBLICATIONS

Liu et al. (Clinical and Experimental Immunology, 2008, vol. 151, p. 441-447).*
Naoumov N et al., Differentiation of Core Gene Products of the Hepatitis B Virus in Infected Liver Tissue Using Monoclonal Antibodies, J Med Virol 53: 127-138 (1997).
Tan, Geok Hun, et al., A phage-displayed single chain variable fragment that interacts with hepatitis B core antigen: Library construction, selection and diagnosis, J Clin Virol 38: 49-56 (2007).
Eren R et al., Preclinical Evaluation of Two Human Anti-Hepatitis B Virus (HBV) Monoclonal Antibodies in the HBV-Trimera Mouse Model and in HBV Chronic Carrier Chimpanzees, Hepatology 32: 588-596 (2000).
Sastry K et al., T Cell Receptor-Like Antibodies Targeting HBV Infected Hepatocytes: A New Tool for Drug Delivery and Pathogenic Studies, J Hepatology 52: S5-S6 (2010) [Abstract 11].
Cohen C et al., Recombinant antibodies with MHC-restricted, peptide-specific, T-cell receptor-like specificity: new tools to study antigen presentations and TCR-peptide-MHC interactions, J Mol Recognition 16: 324-332 (2003).
Naoumov N et al., Targeting Hepatitis B Virus-Infected Cells with a T-cell Receptor-Like Antibody, J Virol 85: 1935-1942 (2011).

* cited by examiner

*Primary Examiner* — Agnieszka Boesen
(74) *Attorney, Agent, or Firm* — Dowell & Dowell, PC

(57) ABSTRACT

There is provided at least one isolated TCR-like antibody or fragment thereof, wherein the antibody or fragment thereof is capable of specifically binding to at least one HBV derived peptide.

3 Claims, 13 Drawing Sheets

A

Ab

CD8 T

Core 18-27

18 19 20 21 22 23 24 25 26 27

F L P S D F F P S V

Anchor residues

Env 183-91

183 184 185 186 187 188 189 190 191

F L L T R I L T I

Anchor residues

B

C

E183/A2 antibody

HEPATITIS B VIRUS SPECIFIC ANTIBODY AND USES THEREOF

FIELD OF THE INVENTION

The present invention relates generally to the field of immune mediated therapies for the detection and treatment of Hepatitis B Virus (HBV) and HBV-related diseases and to methods of preparing these therapies. In particular, the immune mediated therapies may be in the form of HBV specific T cell receptor (TCR)-like antibodies.

BACKGROUND OF THE INVENTION

Hepatitis B Virus (HBV) infection is a major public health problem worldwide, responsible for significant morbidity and mortality from chronic liver disease. It is estimated that there are 350-400 million HBV carriers globally. 75% of chronic HBV patients live in Asia, and approximately 1.5 million people are infected in the United States. Also, despite the availability of effective vaccines, about 50,000-100,000 new cases are reported annually in the United States. The infection is more common in certain risk groups like men who have sex with men, renal dialysis patients and persons with haemophilia, Chronic hepatitis B affects 10-15% of first generation Asian Americans and approximately 5% of children adopted from Russia, Asia and Eastern Europe have chronic hepatitis. Chronic HBV also leads to severe liver diseases including cirrhosis and liver cancer (Hepatocellular Carcinoma), causing more than one million deaths per year.

The treatment for this large reservoir of chronically infected subjects is problematic, since existing drugs suppress but do not eliminate HBV. These drugs have a limited ability in controlling the virus and cause several side effects resulting in the premature discontinuation of their use by many HBV patients.

Clearance of infected hepatocytes requires the presence of virus-specific T cells which are able to secrete anti-viral cytokines. However, these virus-specific T cells are functionally impaired in chronic HBV infected patients. The defect of HBV-specific T cell immunity in these patients is thought to be the reason why a majority of patients experience HBV relapse when therapy is stopped.

80% of Hepatocellular Carcinoma (HCC) is associated with chronic HBV infection, making the 350 million people chronically infected with HBV the largest population at risk for developing HCC. HCC that develops in chronic HBV patients frequently possesses portions of the HBV genome integrated into the tumour cell chromosome resulting in the tumours expressing the viral antigen. Thus HBV antigens can be expressed on HCC cells. Cells infected by these viruses are recognized by the human immune system since the cells expose small peptides derived from the viral proteins in association with Major Histocompatibility complex (MHC)-class 1 molecules on their surface.

TCR-like monoclonal antibodies have been already produced using standard hybridoma approach or by employing phage antibody libraries. However, these antibodies have low binding affinities to their corresponding antigens be it HBV or tumour associated antigens.

SUMMARY OF THE INVENTION

The present invention addresses the problems above, and in particular provides at least one novel antibody that is specific to at least one HBV and/or HBV infected cell.

According to a first aspect, the present invention provides at least one isolated T cell Receptor (TCR)-like antibody or fragment thereof, wherein the antibody or fragment thereof is capable of specifically binding to at least one HBV derived peptide. The HBV derived peptide may comprise at least one hepatitis B core antigen and/or at least one hepatitis B envelope antigen. The HBV derived peptide may be in association with a major histocompatibility complex (MHC)-class 1 molecule.

The antibody may be selected from the group consisting of:
(a) antibody produced by hybridoma cell line PTA-10167 and/or PTA-11068;
(b) antibody having the binding characteristics of the antibody produced by hybridoma cell line PTA-10167 and/or PTA-11068;
(c) antibody that binds to an antigen capable of binding the antibody produced by the hybridoma cell line PTA-10167 and/or PTA-11068;
(d) antibody that binds to an antigen comprising the amino acid sequence of SEQ ID NO:3, SEQ ID NO:24, a variant, mutant or fragment thereof; and
(e) antibody comprising at least one light chain and at least one heavy chain, wherein the light chain comprises amino acid sequence of SEQ ID NO:1, SEQ ID NO:32, a variant, mutant or fragment thereof and the heavy chain comprises amino acid sequence of SEQ ID NO:2, SEQ ID NO:33, a variant, mutant or fragment thereof.

According to another aspect, the present invention provides at least one isolated hybridoma cell line deposited with ATCC (10801 University Blvd., Manassas, Va. 20110) on 2 Jul. 2009 with accession number PTA-10167 and 18 Jun. 2010 with accession number PTA-11068.

According to a further aspect, the present invention provides a method of producing at least one hybridoma, Hepatitis B Virus (HBV)-specific antibody or a fragment therefrom, the method comprising the steps of:
a. immunising at least one non-human mammal with at least one HBV derived peptide in association with a MHC-class 1 molecule, to form at least one B cell specific to the HBV derived peptide in association with a MHC-class 1 molecule;
b. selecting at least one B cell specific to the HBV derived peptide in association with a MHC-class 1 molecule; and
c. fusing the selected B cell with at least one immortalized cell to produce at least one hybridoma, wherein the hybridoma is capable of producing at least one HBV-specific antibody or a fragment thereof specific to the HBV derived peptide in association with a MHC-class 1 molecule; and optionally isolating the HBV-specific antibody from the hybridoma.

According to other aspects, the present invention provides a method of detecting and/or quantifying the presence of HBV, a method of treating HBV and/or at least one HBV-linked disease, the antibody or fragment thereof of the present invention for use as medicine, use of the antibody or fragment thereof of the present invention for the preparation of a medicament, kits, nucleic acids and uses thereof.

BRIEF DESCRIPTION OF THE FIGURES

FIG. 1 (B) is a graph showing that the binding/recognition capacity of c18/A2 mAb was not inhibited by HBeAg.

FIG. 2 (B) is a graph confirming that the sensitivity of c18/A2 mAb approaches that of c18/A2 specific Cytotoxic T lymphocyte (CTL).

FIG. 2 (C) is a graph taken from Gehring A. J et al, 2007 showing the activation of c18/A2 specific CTL with different c18-27 peptide concentrations.

DETAILED DESCRIPTION OF THE INVENTION

Figure 1:
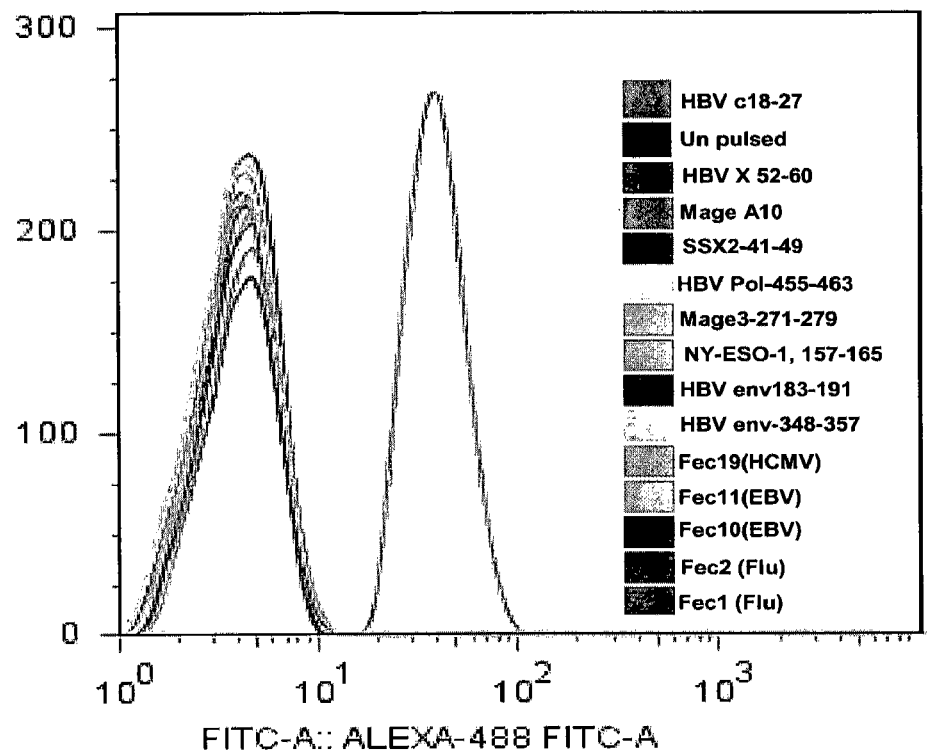
FIG. 1 (A) is a graph of the specificity of c18/A2 mAb where specific staining was observed with c18-27 peptide pulsed cells.
Figure 1:
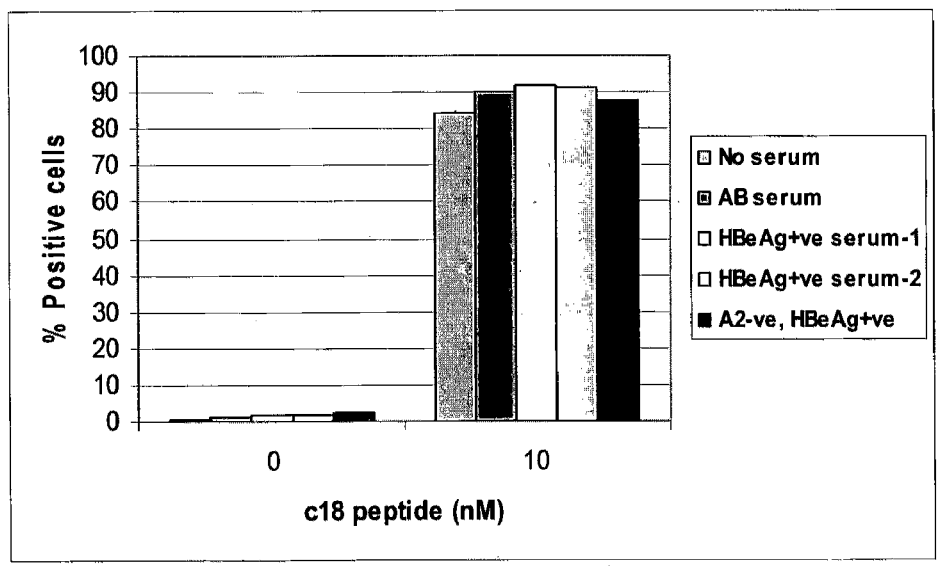

Bibliographic references mentioned in the present specification are for convenience listed in the form of a list of references and added at the end of the examples. The whole content of such bibliographic references is herein incorporated by reference.

Definitions

For convenience, certain terms employed in the specification, examples and appended claims are collected here.

As used herein, the term "antibody" refers to any immunoglobulin or intact molecule as well as to fragments thereof that bind to a specific epitope. Such antibodies include, but are not limited to polyclonal, monoclonal, chimeric, humanised, single chain, Fab, Fab', F(ab)' fragments and/or F(v) portions of the whole antibody. For example, the antibody "c18/A2 mAb" used interchangeably with "HBc18-27 antibody", "antibody against HBc18-27" and "anti-c18/A2 TCR-like antibody" is capable of specifically binding to at least one HBV derived peptide, including but not limited to HBc18-27 (SEQ ID NO:3), or to a variant or fragment thereof, and includes monoclonal antibodies, polyclonal antibodies, single-chain antibodies, and fragments thereof which retain the antigen binding function of the parent antibody. Similarly, the antibody "E183/A2 mAb" used interchangeably with "HBe183-191 antibody", "antibody against HBe183-191" and "anti-e183/A2 mAb TCR-like antibody" is capable of specifically binding to at least one HBV derived peptide, including but not limited to HBe183-191 (SEQ ID NO:24), or to a variant or fragment thereof, and includes monoclonal antibodies, polyclonal antibodies, single-chain antibodies, and fragments thereof which retain the antigen binding function of the parent antibody.

The term "antibody fragment" as used herein refers to an incomplete or isolated portion of the full sequence of the antibody which retains the antigen binding function of the parent antibody. Examples of antibody fragments include Fab, Fab', F(ab')2, and Fv fragments; diabodies; linear antibodies; single-chain antibody molecules; and multispecific antibodies formed from antibody fragments. Fragments of the c18/A2 mAb and E183/A2 mAb are encompassed by the invention so long as they retain the desired affinity of the full-length antibody. In particular, it may be shorter by at least one amino acid. For example, the fragment of a c18/A2 mAb antibody comprises the antigen binding function that enables it to bind to HBc18-27 (SEQ ID NO:3), or to a variant or fragment thereof and the fragment of a E183/A2 mAb antibody comprises the antigen binding function that enables it to bind to HBe183-191 (SEQ ID NO:24), or to a variant or fragment thereof.

The term "antigen" as used herein, refers to a substance that prompts the generation of antibodies and can cause an immune response. It may be used interchangeably in the present invention with the term "immunogen". In the strict sense, immunogens are those substances that elicit a response from the immune system, whereas antigens are defined as substances that bind to specific antibodies. An antigen or fragment thereof may be a molecule (i.e. an epitope) that makes contact with a particular antibody. When a protein or a fragment of a protein is used to immunize a host animal, numerous regions of the protein may induce the production of antibodies (i.e. elicit the immune response), which bind specifically to the antigen (given regions or three-dimensional structures on the protein). The antigen may include but is not limited to HBc18-27 used interchangeably with "HBc18-27 peptide" and "c18/A2", HBe183-191 used interchangeably with "HBe183-191 peptide" and "E183/A2" and fragments thereof.

The term "comprising" is herein defined to be that where the various components, ingredients, or steps, can be conjointly employed in practicing the present invention. Accordingly, the term "comprising" encompasses the more restrictive terms "consisting essentially of" and "consisting of." With the term "consisting essentially of" it is understood that the epitope/antigen of the present invention "substantially" comprises the indicated sequence as "essential" element. Additional sequences may be included at the 5' end and/or at the 3' end. Accordingly, a polypeptide "consisting essentially of" sequence X will be novel in view of a known polypeptide accidentally comprising the sequence X. With the term "consisting of" it is understood that the polypeptide, polynucleotide and/or antigen according to the invention corresponds to at least one of the indicated sequence (for example a specific sequence indicated with a SEQ ID Number or a homologous sequence or fragment thereof).

The term "derivative," as used herein, refers to the chemical modification of at least one HBV derived peptide, or a polynucleotide sequence encoding at least one HBV derived peptide, or of a polynucleotide sequence complementary to a polynucleotide sequence encoding at least one HBV derived peptide. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The phrase "HBV derived peptide" refers to a protein/peptide that may be derived from HBV. In particular, the HBV derived peptide may include but is not limited to the core antigen, envelope antigen, surface antigen and/or mutants thereof. More in particular, the HBV-derived peptide may be HBc18-27 and/or HBe183-191.

The term "HBc18-27" is herein defined as an epitope that can stimulate HLA class I restricted T cells and is used interchangeably with "c18/A2". The sequence of the epitope may be "FLPSDFFPSV" (SEQ ID NO:3). In the present invention, the term HBc18-27 is used to refer to the HBc18-27 epitope of genotype A/D prevalent amongst Caucasians of sequence SEQ ID NO:3 unless otherwise stated.

The term "HBe183-191" is herein defined as an epitope that can stimulate HLA class I restricted T cells and is used interchangeably with "E183/A2". The sequence of the epitope may be "FLLTRILTI" (SEQ ID NO:24).

The term "fragment' as used herein, refers to an incomplete or isolated portion of the full sequence of at least one HBV derived peptide which comprises the active site(s) that confers the sequence with the characteristics and function of the peptide. In particular, it may be shorter by at least one nucleotide or amino acid and may be an immunogenic fragment. For example a fragment of HBc18-27 comprises the active site(s) that enable the c18/A2 mAb or fragment thereof to recognise and/or a fragment of HBe183-191 comprises the active site(s) that enable the E183/A2 mAb or fragment thereof to recognise. A fragment may also refer to a fragment of an antibody according to any aspect of the present invention where the antibody comprises the active site that recognises the corresponding antigen. The fragment may at least be 10 amino acids in length.

The term "humanized antibody," as used herein, refers to at least one antibody molecule in which the amino acid sequence in the non-antigen binding regions has been altered so that the antibody more closely resembles a human antibody, and still retains its original binding ability.

As used herein, the term "hybridoma" refers to cells that have been engineered to produce a desired antibody in large amounts. For example to produce at least one hybridoma, B cells are removed from the spleen of an animal that has been challenged with the relevant antigen and fused with at least one immortalized cell. This fusion is performed by making the cell membranes more permeable. The fused hybrid cells (called hybridomas), will multiply rapidly and indefinitely and will produce at least one antibody. An example of a hybridoma cell line produced according to the method of the present invention includes but is not limited to c18/A2 mAb#1 which produces monoclonal antibody to HBc18-27, c18/A2 mAb.

"Immortalised cells" as used herein are also known as transformed cells—i.e. cells whose growth properties have been altered. This does not necessarily mean that these are "cancer" or "tumour" cells, i.e. able to form a tumour if introduced into an experimental animal, although in some cases they may do. Immortalised cell lines include but are not limited to NS1, Jurkat, HeLa, HepG2, SP2/0, Hep-3b and the like.

The term "isolated" is herein defined as a biological component (such as a nucleic acid, peptide or protein) that has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been isolated thus include nucleic acids and proteins purified by standard purification methods. The term also embraces nucleic acids, peptides and proteins prepared by recombinant expression in a host cell as well as chemically synthesized nucleic acids.

The term "monomer" used in the present invention comprises at least one antigen, a heavy chain and/or light chain. For example, in the present invention, the monomer used in Example 1, comprises HBc18-27 and at least one HLA heavy and light chain. In particular, the monomer may comprise SEQ ID NO:3 or fragment thereof, a heavy and a light chain. The term "monomer" may be used interchangeably in the present invention with the term "c18/A2 complex" and "c18/A2 monomer".

The term "mutant" of a HBV derived peptide is herein defined as one which has at least one amino acid sequence that varies from at least one reference virus-encoded sequence via substitution, deletion or addition of at least one amino acid, but retains the ability to bind and activate the antibody of the present invention and be activated by the non-mutated peptide. Examples of mutants of HBc18-27 may include but are not limited to SEQ ID NOs: 4 to 16 as provided in Table 2.

The term "sample," as used herein, is used in its broadest sense. A biological sample suspected of containing nucleic acids encoding at least one HBV derived peptide, or fragments thereof, or at least one HBV derived peptide itself may comprise a bodily fluid, an extract from a cell, chromosome, organelle, or membrane isolated from a cell, a cell; genomic DNA, RNA, or cDNA (in solution or bound to a solid support), a tissue, a tissue print; and the like.

As used herein, the terms "specific binding" or "specifically binding" refer to the interaction between a protein or peptide and an agonist, an antibody, or an antagonist. In particular, the binding is between an antigen and an antibody. The interaction is dependent upon the presence of a particular structure of the protein recognized by the binding molecule (i.e., the antigen or epitope). For example, if an antibody is specific for epitope "A", the presence of a polypeptide containing the epitope A, or the presence of free unlabeled A, in a reaction containing free labeled A and the antibody will reduce the amount of labeled A that binds to the antibody. For example, c18/A2 mAb may specifically bind the antigen, HBc18-27 and E183/A2 mAb may specifically bind the antigen, HBe183-191.

The term "subject" is herein defined as vertebrate, particularly mammal, more particularly human. For purposes of research, the subject may particularly be at least one animal model, e.g., a mouse, rat and the like.

The term "TCR-like monoclonal antibody" as used herein refers to at least one antibody that behaves similarly to a T cell receptor (TCR) antibody. In particular, the TCR-like monoclonal antibody may refer to an antibody that can recognize MHC-bound peptides. An example of a TCR-like monoclonal antibody may include but is not limited to c18/A2 mAb and E183/A2 mAb.

A "variant" of at least one HBV derived peptide, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted; or deleted without abolishing biological or immunological activity may be found using computer programs well known in the art, for example, DNASTAR software.

A person skilled in the art will appreciate that the present invention may be practised without undue experimentation according to the method given herein. The methods, techniques and chemicals are as described in the references given or from protocols in standard biotechnology and molecular biology text books.

In one aspect of the present invention, there is provided at least one isolated T Cell Receptor (TCR)-like antibody or fragment thereof, wherein the antibody or fragment thereof may be capable of specifically binding to at least one HBV derived peptide. The HBV derived peptide may comprise at least one hepatitis B core antigen and/or at least one hepatitis B envelope antigen. This new antibody may have the potential to target HBV infected cells and HBV derived Hepatocellular Carcinoma (HCC) cells based on these cells intracellular expression of signature antigens and their association with human MHC class I (specifically on a form termed Human Leukocyte Antigen—HLA-A201). The HBV derived peptide may be in association with a major histocompatibility complex (MHC)-class I molecule, in particular a HLA class I molecule. The HLA class I molecule may be HLA-A2. More in particular, the HBV derived peptide may be part of an MHC-I peptide complex, the complex comprising the HBV derived peptide and a HLA class I molecule.

MHC-class I proteins are collectively termed HLA in humans and are expressed on the surface of nearly all nucleate cells of the human body, and they bind small peptides (usually 9-10 amino acids long) derived form the endogenously produced viral or self altered (tumour) proteins in the endoplasmic reticulum to produce complexes. The complex of HLA-class I protein and their bound peptides is transported to the surface of the infected cells where it can be recognized by the T cell receptor present on cytotoxic CD8 T lymphocytes. Different HLA types include HLA-A, HLA-B, HLA-C, HLA-DPA1, HLA-DPB1, HLA-DQA1, HLA-DQB1, HLA-DRA, and HLA-DRB1.

The specific interaction between the T cell receptor present on cytotoxic CD8 T lymphocytes and the viral peptides presented by the HLA-class I molecules activate the CD8 T cells that can destroy viral infected cells or produce antiviral cytokines (TNF-alpha and IFN-gamma) that are able to clear non-cytopatically virus infected cells.

Viral proteins produced within the infected cells are not accessible to the classical antibody, but the immune system recognizes viral infected cells through the T cell receptor present on CD8 T lymphocytes. Since production of virus-specific CD8 T cells requires a high degree of technical proficiency and such cells are extremely unstable in vitro, the production of antibodies that specifically recognizes the HLA-restricted viral peptide ligand on the surface of virus-infected cells would allow the detection of virus infected cells in vivo in humans and then potentially the delivery of moieties with therapeutic or diagnostic potential.

Since the HLA-class I/viral peptide complexes are usually different in different individuals, different TCR-like antibodies will act only in a selected population of humans carrying a defined HLA-class I molecules. The HLA-class I molecules are produced by a complex of genes located on human chromosome 6 and these genes have diversified to greater extend, thus every single individual might present a particular combination of different HLA-class I proteins. The molecular structure of the different HLA-class I molecules select for different viral peptides and thus there is an extreme diversification of the HLA-class I viral peptide complexes presented on infected cells.

About 50% of the human population expresses the HLA-class I molecule HLA-A2, which represent a family of HLA-class I molecules produced by gene products of many HLA-A*02 alleles, comprising HLA-A*0201, *0202, *0203, *0206, and *0207 gene products. There are distinct differences in the subtypes between Caucasian and Asian populations. Whereas more than 95% of the HLA-A2 positive Caucasian population is HLA-A0201 the HLA-A2 positive, the Chinese population can be broken down into 23% HLA-A0201; 45% HLA-A0207; 8% HLA-A0206; 23% HLA-A0203.

The TCR-like antibodies according to any aspect of the present invention may target a HBV derived peptide presented by different alleles of HLA-A2 molecules and thus it may target about 50% of human population infected by HBV. The TCR-like antibodies according to any aspect of the present invention have the specificity similar to that of the naturally occurring T cell receptor of the virus-specific CD8 T lymphocytes which are able to recognize virus-infected cells and thus can be called T cell receptor (TCR)-like antibodies.

The TCR-like antibodies according to any aspect of the present invention, have relatively high binding affinities to their corresponding MHC-peptide complexes, and thus are able to recognize naturally occurring virus infected cells which often display a very low quantity of viral peptide/HLA-class I ligands on their surface. These TCR-like antibodies are also able to recognize HBV-infected human hepatocytes.

The HBV derived peptide may comprise at least one hepatitis B core antigen, envelope antigen, surface antigen and/or mutants thereof. In particular, the HBV derived peptide may comprise at least one hepatitis B core antigen and/or hepatitis B envelope antigen. In particular, the HBV derived peptide may comprise, consists of or consists essentially of HBc18-27 and/or HBe183-191, a variant, mutant or fragment thereof. Even more in particular, HBc18-27 comprises, consists of or consists essentially of SEQ ID NO:3, a variant, mutant, or fragment thereof and HBe183-191 comprises, consists of or consists essentially of SEQ ID NO:24, a variant, mutant, or fragment thereof. The antibodies of the present invention may bind to the c18/A2 and/or E183/A2 monomer(s) on the surface of HBV infected cells and tumour cells and target them for immune mediated lysis (i.e. Antibody Dependent Cellular Cytotoxicity (ADCC) by Natural Killer Cells).

The antibody may be selected from the group consisting of:
(a) antibody produced by hybridoma cell line PTA-10167 and/or PTA-11068;
(b) antibody having the binding characteristics of the antibody produced by hybridoma cell line PTA-10167 and/or PTA-11068;
(c) antibody that binds to an antigen capable of binding the antibody produced by the hybridoma cell line PTA-10167 and/or PTA-11068;
(d) antibody that binds to an antigen comprising the amino acid sequence of SEQ ID NO:3, SEQ ID NO:24, a variant, mutant or fragment thereof; and
(e) antibody comprising at least one light chain and at least one heavy chain, wherein the light chain comprises amino acid sequence of SEQ ID NO:1, SEQ ID NO:32, a variant, mutant or fragment thereof and the heavy chain comprises amino acid sequence of SEQ ID NO:2, SEQ ID NO:33, a variant, mutant or fragment thereof.

The antibody may be at least one human, humanized or chimeric antibody. The antibody may be a mouse IgG1 (with kappa light chain), that may be able to target HBV infected cells with high specificity since it targets the HLA-A201-HBV core 18-27 complex and/or HLA-A201-HBV envelope 183-191 complex present exclusively on the surface of HBV infected cells.

Techniques developed for the production of "chimeric antibodies" (Morrison, et al., 1984 incorporated herein by reference in their entirety) by splicing the genes from a mouse antibody molecule of appropriate antigen specificity together with genes from a human antibody molecule of appropriate biological activity can be used. For example, the genes from a mouse antibody molecule specific for an autoinducer can be spliced together with genes from a human antibody molecule of appropriate biological activity. A chimeric antibody is a molecule in which different portions are derived from different animal species, such as those having a variable region derived from a murine mAb and a human immunoglobulin constant region.

In addition, techniques have been developed for the production of humanized antibodies (See, e.g., U.S. Pat. No. 5,585,089 and/or U.S. Pat. No. 5,225,539, which are incorporated herein by reference in their entirety). An immunoglobulin light or heavy chain variable region consists of a "framework" region interrupted by three hypervariable regions, referred to as complementarity determining regions (CDRs). Briefly, humanized antibodies are antibody molecules from non-human species having one or more CDRs from the non-human species and a framework region from a human immunoglobulin molecule.

The antibody may be labelled with at least one radionuclide and/or fluorochrome in order to improve targeting of HBV infected tumour cells in vivo in at least a diagnostic and/or therapeutic capacity. For example, detecting HBV infected HCC cells by Positron Emission Tomography (PET). The antibody labeled with the radionuclide may enable better targeting of the diseased cells for surgery and/or radiotherapy. The antibody may be further labelled with at least one toxin and/or chemotherapeutic reagent. In particular, the labelled antibody may be used as an 'immunotoxin' that better targets these toxic agents to tumour cells.

The TCR-like antibodies of any aspect of the present invention may also be used to directly quantify the number and location of peptide/HLA class I complex on infected cells or any antigen presenting cell and thus can be useful to evaluate the efficiency of processing and presentation of HBV antigens in different cell types.

The antibody may recognize c18-27 and/or env183-91 peptide(s) in the context of HLA-A201. This TCR-like mAb may represent a new, valuable tool in two major areas of HBV immunology. First, this mAb can be used to detect and directly visualize the presence of pMHC complexes by standard methods of flow cytometry and immunohistochemistry. It may be useful for the study and analysis of antigen presentation by determining the expression of pMHC on APCs, hepatocellular carcinoma tumour cells and lymphoid cells. Questions relating to how and where certain events occur during antigen presentation may be directly addressed and the expression of T cell epitopes on the APC may be visualized and quantified.

The antibodies according to any aspect of the present invention may open new opportunities for use as targeting moieties for various antibody-based immunotherapeutic approaches. The TCR-like mAb can be linked with a drug and the resulting 'ab-conjugate' can be used to deliver the drug to the infected cells.

In particular, the antibody may be linked with at least one drug, anti-viral drug, toxin, and/or chemotherapeutic reagent. In particular, the antibodies may be used to deliver drugs to the infected hepatocytes with a high degree of specificity to suppress viral infections and tumours. The drugs may include but are not limited to IFN-alpha, TLR-agonist, adefovir, entecavir, lamivudine, remofovir, telbivudine, tenofovir, and the like. The antibody of the present invention linked with at least one anti-viral drug, may increase the drug availability for HBV infected cells which may enhance the IFN-alpha effect for the infected cells whilst reducing systemic IFN-alpha exposure, thus reducing side effects usually caused by the anti-viral drugs. This may lead to a new treatment for chronic HBV, possibly preventing liver cancer and other complications associated with HBV.

The c18/A2 mAb and/or E183/A2 mAb may be linked with at least one traceable agent and may be potentially used to quantify HBV infected hepatocytes in vitro or in vivo. The traceable agent may be any biological or chemical component which is traceable. The traceable agent may include, but is not limited to environmental agents, blood markers, antigens, pesticides, drugs, chemicals, toxins, PCBS, PBBS, lead, neurotoxins, blood electrolytes, metabolites, analytes, NA+, K+, CA+, urea nitrogen, creatinine, biochemical blood markers and components, ChE, AChE, BuChe, tumour markers, PSA, PAP, CA 125, CEA, AFP, HCG, CA 19-9, CA 15-3, CA 27-29, NSE, hydroxybutyrate, acetoacetate, anti-malarial drugs such as amodiaquine, artemether, artemisinin, artesunate, atovaquone, cinchonine, cinchonidine, chloroquine, doxycycline, halofanthne, mefloquine, primaquine, pyrimethamine, quinine, quinidine, and sulfadoxine; antibiotic drugs such as ampicillin, azithromycin, doxycycline, erythromycin, penicillin, and tetracycline; anti-retroviral drugs such as abacavir, adefovir, didanosine, entecavir, indinavir, lamivudine, nevirapine, remofovir, ritonavir, saquinavir mesylate, telbivudine, tenofovir, zalcitabine, and zidovudine.

The TCR-like mAb according to any aspect of the present invention may be used in patients with hepatocellular carcinoma (HCC). The integration of the HBV genome into infected cells is the most consistently associated factor in malignancy of HCC. The TCR-like mAb can be used to address the antigen presentation studies on liver biopsies of HCC patients. The immuno-conjugate prepared from TCR-like mAb, linked to at least one drug might have the capacity to kill cancer cells. This approach to HBV immunotherapy may lead to clinical applications that improve treatment of HBV patients with minimal residual side-effects.

The c18/A2 mAb and E183/A2 mAb can be used to obtain precise information about presence, expression pattern and distribution of the pMHC complexes on viral-infected cell surface, and on professional antigen presenting cells. Direct tracking of antigen presenting cells in vitro and in vivo may also be carried out with the c18/A2 mAb and/or E183/A2 mAb. The c18/A2 mAb and E183/A2 mAb may also be used for conjugation of c18/A2 mAb and E183/A2 mAb respectively with antiviral cytokines or toll-like receptors or antiviral drugs for targeted delivery of immunoconjugates to infected cells as a new immunotherapeutic strategy. The humanized mAb-drug conjugate may have the potential to target hepatocellular carcinoma arising in HBV infected patients which express viral antigens. The mAb can be also used as a diagnostic reagent by linking it with a suitable fluorochrome or radionuclide.

According to yet another aspect, the present invention provides at least one method of producing at least one hybridoma, Hepatitis B Virus (HBV)-specific antibody or a fragment therefrom, the method comprising the steps of:
a. immunising at least one non-human mammal with at least one HBV derived peptide in association with a MHC-class I molecule, to form at least one B cell specific to the HBV derived peptide in association with a MHC-class I molecule;
b. selecting at least one B cell specific to the HBV derived peptide in association with a MHC-class I molecule; and
c. fusing the selected B cell with at least one immortalized cell to produce at least one hybridoma, wherein the hybridoma is capable of producing at least one HBV-specific antibody or a fragment thereof specific to the HBV derived peptide in association with a MHC-class I molecule; and
optionally isolating the HBV-specific antibody from the hybridoma.

Step (b) according to the method of the present invention may comprise incubating at least one B cell specific to the HBV derived peptide in association with a MHC-class I molecule with:
i. at least one biotinylated antigen, the antigen capable of binding the B cell specific to the HBV derived peptide in association with a MHC-class I molecule; and
ii. at least one anti-biotin conjugated bead.

This novel method of production of hybridoma, HBV-specific antibody or a fragment therefrom, allows for the development of TCR-like HLA/HBV specific monoclonal antibodies, with a higher degree of reliability than has been previously possible. For the preparation of at least one HBV-specific antibody of the present invention, any technique that provides for the production of antibody molecules by continuous cell lines in culture may be used provided a step of selection of B cell specific to the antigen is carried out before the fusion with the immortalised cell. Even more in particular, step (b) may be carried out using Magnetic-activated cell sorting (MACS) of Miltenyi Biotec, Singapore.

The HBV derived peptide may comprise, consists of or consists essentially of the amino acid sequence of SEQ ID NO:3, SEQ ID NO:24, a variant, mutant or fragment thereof.

An example of the method used for the production of the antibody of the present invention is given in Example 1. Example 1 provides a method used for the production of monoclonal antibody specific for a peptide of SEQ ID NO:3 derived from the core antigen of HBV using BALB/c mice.

According to another aspect, the present invention provides at least one isolated antibody or fragment thereof, produced according to any method of the present invention.

According to yet another aspect, the present invention provides a method of detecting and quantifying the presence and distribution of at least one HBV infected cell in a subject, the method comprising:
a. contacting at least one antibody or fragment thereof according to any aspect of the present invention with at least one sample obtained from at least one subject; and
b. detecting and quantifying binding of the antibody to the HBV infected cell.

The antibody may bind specifically to HBc18-27, HBe183-191, a variant, mutant or fragment thereof or a fragment thereof of the HBV infected cell. The binding confirms that the cell may be HBV infected, the sample comprises at least one HBV infected cell and/or the subject may be HBV positive. More in particular, the method may be an in vitro method of detection and quantification.

According to another aspect, the present invention provides a method of detecting HBV-linked Hepatocellular Carcinoma (HCC) cell in a subject, the method comprising:
a. contacting at least one antibody or fragment thereof according to any aspect of the present invention with at least one sample obtained from at least one subject; and
b. detecting binding of the antibody to the HBV-linked HCC infected cell.

The method of detecting and quantifying according to any aspect of the present invention may be a non-invasive method of diagnosis and may also be used for studying several immunological aspects of HBV. The method may be used to detect and directly visualize the presence of phenotypic analysis of antigen (pMHC) complexes by standard methods of flow cytometry and immunohistochemistry for the study and analysis of antigen presentation by determining the expression of pMHC on APCs, HCC tumour cells and lymphoid cells. This method may be useful for determining the presence of and the reasons behind certain events that occur during antigen presentation and the expression of T cell epitopes on the APC may be visualized and quantitated.

According to another aspect, the present invention provides at least one method of treatment of HBV and/or at least one HBV-linked disease, the method comprising administering to a subject in need thereof at least one antibody or a fragment thereof according to any aspect of the present invention. The antibody of the present invention may be administered in combination with other similar antibodies targeting different HBV peptides in association with different HLA-types. The tumour cells and viruses may thus be given no opportunity to adapt to this form of therapy.

According to another aspect, the present invention provides at least one antibody or a fragment thereof according to any aspect of the present invention for use in medicine.

According to yet another aspect, the present invention provides at least one use of the antibody or a fragment thereof according to any aspect of the present invention for the preparation of a medicament for treatment of HBV and/or at least one HBV-linked disease. BV-linked diseases include cirrhosis, HCC and the like. Chronic HBV accounts for over 75% of all HCC.

According to yet another aspect, the present invention provides at least one kit for diagnosing HBV and/or at least one HBV-linked disease, the kit comprising at least one antibody or a fragment thereof of the present invention.

According to one aspect, the present invention provides at least one isolated nucleic acid molecule encoding
(a) at least one light chain of the antibody or a fragment thereof according to any aspect of the present invention wherein the light chain comprises SEQ ID NO:1, SEQ ID NO:32, a variant, mutant or fragment thereof; and/or
(b) at least one heavy chain of the antibody or a fragment thereof according according to any aspect of the present invention, wherein the heavy chain comprises SEQ ID NO:2, SEQ ID NO:33, a variant, mutant or fragment thereof.

According to another aspect, the present invention provides a method of determining the efficacy of a vaccine in a subject, the method comprising:
 contacting at least one antibody or fragment thereof according to any aspect of the present invention with at least one sample obtained from the subject between 5 and 15 days following administration of the vaccine; and
 detecting binding of the antibody or fragment thereof to a HBV infected cell; and
 comparing the number of HBV infected cells before and after administration of the vaccine, wherein a decrease in the number of HBV infected cells indicates an efficacious vaccine.

The determining of the presence of HBV antigens in HCC cells may be used to test antigen processing of vaccines or defects of antigen processing in different individuals. The TCR-like antibodies according to any aspect of the present invention may also be utilized for vaccine validation, as a useful tool to determine whether desired HBV-T cell epitopes are displayed on cells and as research reagents to understand the fate of antigen processing and presentation in vivo and in vitro, and these processes could be evaluated between solid tumour cells, metastatic tumour cells, cells exposed to chemo-agents, tumour cells after exposure to a vaccine, and the like.

According to another aspect, the present invention provides a method for determining the accuracy of antigen processing and presentation in a cell, the method comprising the step of contacting at least one antibody or fragment thereof according to any aspect of the present invention with the cell.

According to another aspect, the present invention provides an expression vector comprising the nucleic acid of the present invention and a host cell comprising the expression vector. In particular, the vectors may comprise, but not limited to, lentiviral vectors, retroviral vectors, adenoviral vectors, adeno-associated virus vectors, and Herpes Simplex Virus vectors. More in particular, retroviral vectors may be used for delivery of the constructs either in vitro, ex vivo or in vivo.

The TCR-like antibodies according to any aspect of the present invention may be used as therapeutic agents, either as an antibody or bispecific molecule/bispecific antibiody, or may be used as vehicles for drug transport to transport payloads of toxic substances to tumour cells and/or viral infected cells.

The TCR-like antibodies according to any aspect of the present invention may also be used for carcinogenic profiling, to provide an individualized approach to cancer detection and treatment. Accordingly, the term "carcinogenic profiling" refers to the screening of cancer cells with TCR-like antibodies to define whether HBV-peptide presented by HLA class I molecules are displayed on the surface of HCC.

Having now generally described the invention, the same will be more readily understood through reference to the following examples which are provided by way of illustration, and are not intended to be limiting of the present invention.

A person skilled in the art will appreciate that the present invention may be practised without undue experimentation according to the method given herein. The methods, techniques and chemicals are as described in the references given or from protocols in standard biotechnology and molecular biology text books.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Example 1

Preparation of Antigen/Monomer

The HBV antigen targeted was HBc18-27 of FLPSDFF-PSV (SEQ ID NO:3). The monomer prepared was an FPLC purified recombinant, membrane free, fully folded, heterotrimeric complex of at least one HLA-A201 heavy and light chain plus an antigenic peptide of SEQ ID NO:3.

Human Major Histocompatibility Complex (MHC) Class-I HLA-A201 heavy chains (HC) and light chains (LC) (B2 Microglobulin) were expressed as recombinant proteins in BL21 *E. coli* (Novagen, Germany). The heavy and light chains were isolated as inclusion bodies and dissolved in 8M urea.

The antigenic peptide of SEQ ID NO:3 from HBc18-27 of HBV was then selected and refolded with the HLA heavy and light chains to form c18/A2 monomers in vitro. Anion-exchange chromatography was used to purify the monomers. c18/A2 monomers were then tetramerised.

Generation of Anti-c18/A2 TCR-Like Antibodies

The c18/A2 monomers of the step above were used as a source of antigen to stimulate antibody responses in immunized Balb/C mice. Female Balb/c mice were immunised with 25 μg of purified c18/A2 monomers in Complete Freunds i.p. (primary dose) (Sigma-Aldrich, USA) then boosted with the same monomer plus Incomplete Freunds (3 booster doses) (Sigma-Aldrich, USA). A final booster dose without adjuvant was performed by tail injection 3 days before fusion with NS1 myeloma cells.

The mice were euthanised and splenocytes prepared by gentle homogenisation. B cells with the desired specificity were purified by incubating the splenocytes with biotinylated c18/A2 monomers which bind to specific B cell receptors found on the surface of the B cell specific to the monomer. Then anti-Biotin conjugated immuno-Magnetic beads (Miltenyi-Biotec, Singapore) was used to positively select the bound B-cells on magnetic columns via immunomagenetic selection. Pre-purifying the antigen specific B cells prior to myeloma fusion from the immunized mice, using a biotinylated form of the monomer linked to an immunomagnetic bead greatly improved the percentage of hybridomas that have the correct specificity compared to standard hybridoma approaches.

The selected B cells were fused by PEG1500 (Sigma-Aldrich, USA) with NS1 myeloma cells (kindly provided by Professor Chan Soh Ha of National University of Singapore, Singapore). using standard technique. The resulting hybridoma cell mixture was seeded in 96-well plates and selected in HAT medium (Sigma-Aldrich, USA) for 2 weeks. About 1500 hybridomas were screened for the selection of desired mAb specificity by flow cytometry. Either c18-27 peptide of SEQ ID NO:3 pulsed or an M1 peptide of SEQ ID NO:17 (GILGFVFTL) pulsed C1R cells were incubated with the hybridoma supernatants for 30 min at 4° C., washed and further incubated with anti-mouse IgG-alexafluor-488 secondary antibodies (Invitrogen, USA) for 30 min at room temperature, washed and analyzed on BD FACSCAN flow cytometer using cell quest software. Only one clone (i.e. c18/A2 mAb#449) displayed the required recognition characteristics restricted to c18/A2 monomers and did not show reactivity with M1 peptide pulsed cells. This positive clone was sub-cloned twice by limiting dilution, stably expanded and the culture supernatants were collected in bulk. The c18/A2 mAb from these supernatants were purified by Protein G Agarose column.

Specificity of c18/A2 mAb

The specificity of c18/A2 mAb was tested by incubating T2 cells obtained from ATCC with different HLA-A2 restricted peptides derived from HBV polymerase, X and envelope proteins as well as from EBV, flu (in particular H1N1), CMV and a wide variety of tumour associated antigen epitopes. Sequences (i.e. SEQ ID NOs: 17-29) of the peptides used are provided in Table 1. T2 cells were incubated with 1 μM each of the peptides for 1 hr, washed 3 times and stained with 0.5 μg of c18/A2 mAb. After washing 3 times, the cells were incubated with anti-mouse IgG-AlexaFluor488 antibody (Invitrogen, USA) for 30 min, washed and acquired on a flow cytometer.

TABLE 1

Peptides used for specificity testing of HBc18/A2 mAb as shown in FIG. 1A

| Peptide | Sequence | SEQ ID NO: |
|---|---|---|
| M1 peptide/FEC1 (Flu) | GILGFVFTL | 17 |
| HBV X, 52-60 | HLSLRGLPV | 18 |
| Mage A10, 254-262 | GLYDGMEHL | 19 |
| SSX2, 41-49 | KASEKIFYV | 20 |
| HBV pol, 455-463 | GLSRYVARL | 21 |
| Mage3, 271-279 | FLWGPRALV | 22 |
| NY-ESO-1, 157-165 | SLLMWITQA | 23 |
| HBV env, 183-191 | FLLTRILTI | 24 |
| HBV env, 348-357 | GLSPTVWLSV | 25 |
| FEC19 (HCMV) | NLVPMVATV | 26 |
| FEC11 (EBV) | GLCTLVAML | 27 |
| FEC10 (EBV) | CLGGLLTMV | 28 |
| FEC2 (Flu) | FMYSDFHFI | 29 |

As shown in the FIG. 1A, c18/A2 mAb reacted specifically with c18-27 pulsed cells and did not stain any cells which were pulsed with any other peptides. Similarly, c18/A2 mAb did not recognize any peptide alone or HLA-A2 alone as pre-incubation of the antibody with any peptide did not result in the decreased staining of cells pulsed with c18-27 peptide.

To determine if c18/A2 mAb retains its binding capacity even in the presence of patient's sera components and viral antigens, c18/A2 mAb was pre-incubated with 100 μl of sera of 3 different HBeAg+ patients (kindly provided by Dr. Lim Seng Gee, National University Hospital, Singapore) separately and with the sera of healthy individuals (AB serum, from Invitrogen). This pre-incubated c18/A2 mAb-sera mixture was used to stain c18-27 peptide pulsed T2 cells. FIG. 1B demonstrates that pre-incubation of c18/A2 mAb with HBeAg+ sera had no inhibitory effect on the recognition of c18/A2 complexes by c18/A2 mAb. Taken together, these results clearly demonstrated that peptide specific and MHC-restricted antibodies (i.e. c18/A2 mAb) exhibited as good specificity as a T Cell Receptor and the c18/A2 mAb binding capacity was not perturbed by HBeAg.

Sensitivity of c18/A2 mAb

Figure 2:
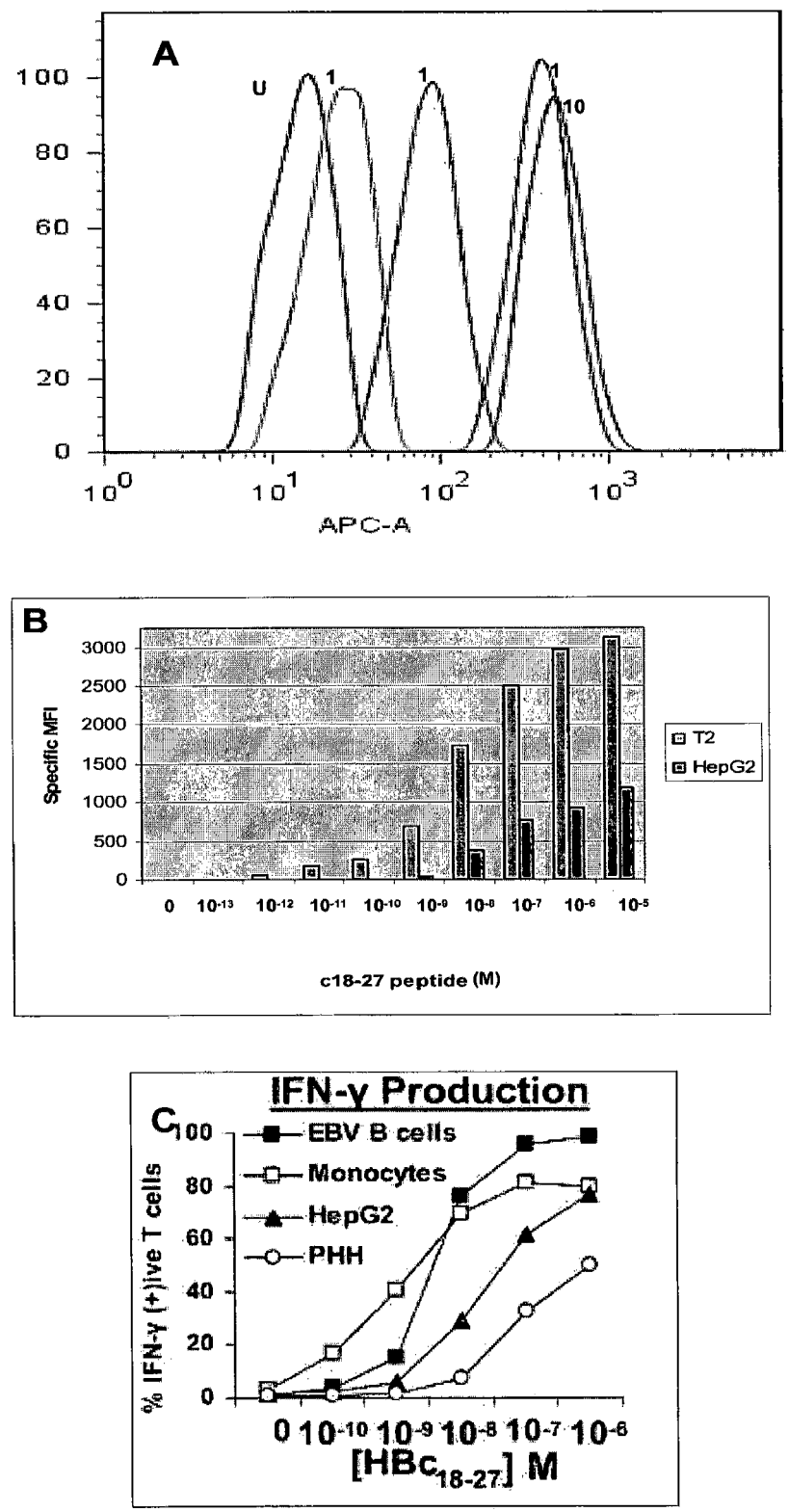
FIG. 2 (A) is a graph showing that a minimal concentration of c18-27 peptide was needed for detection by c18/A2 mAb. As low as 1 pM of c18-27 peptide was sufficient to achieve significant staining.

To find out the minimal peptide concentration required to achieve significant staining with c18/A2 mAb, T2 cells were incubated for 1 hr with various concentrations of c18-27 peptide of SEQ ID NO:3 and subsequently stained with c18/A2 mAb. As shown in FIG. 2A, as low as 1 μM of the c18-27 peptide was sufficient to achieve the significant staining. Cells were acquired on a FACS Canto flow cytometer and the level of fluorescent intensity of cells analyzed with Flow Jo software.

In order to investigate whether the c18/A2 mAb could detect c18/A2 complexes with the same sensitivity as the TCR of T cells specific for c18/A2 complexes, T2 and HepG2 cells obtained from ATCC were incubated with various concentrations of c18-27 peptide for 1 hr and washed. Cells were stained with c18/A2 mAb followed by incubation with anti-mouse IgG-Alexafluor488 antibodies (Invitrogen, USA). A total of 10,000 events were recorded using FACS Canto Flow cytometer. Isotype values were subtracted to achieve specific mean fluorescent intensity. As shown in FIG. 2B, the minimal c18-27 peptide concentrations of 1 pM and 1 nM were required for EBV-B cells and HepG2 cells, respectively, for significant staining with c18/A2 mAb. These results were similar to the concentrations that were reported to be required to activate (IFN-γ production) the minimum number of c18/A2 specific Cytotoxic T lymphocyte (CTL) as shown in FIG. 2C taken from Ghering et al., 2007. The c18/A2 mAb was thus shown to recognise pMHC complexes with a sensitivity similar to that of c18/A2 specific CTL.

Affinity of c18/A2 mAb

Figure 3:
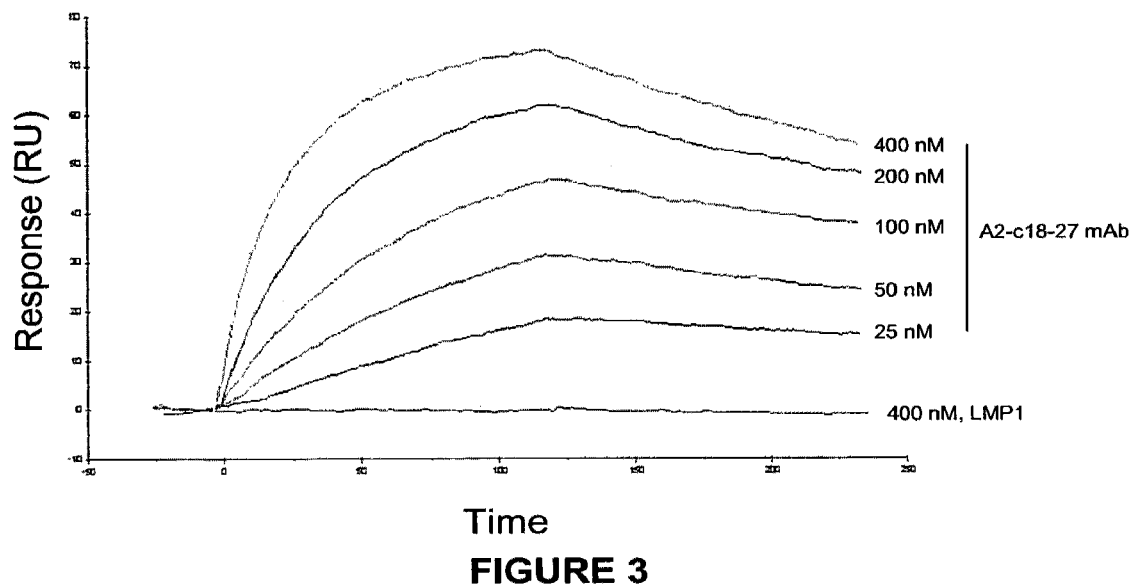
FIG. 3 is a graph of the results of a BIAcore analysis of c18/A2 mAb. Binding of monomer to c18-A2 mAb occurred with on- and off-rates of $1.1 \times 10^5$ $M^{-1} \cdot S^{-1}$ and $2.5 \times 10^{-3}$ $M^{-1} \cdot S^{-1}$, respectively, resulting in a $K_D (K_{off}/K_{on})$ of 22.6 nM.

The affinity of c18/A2 mAb was determined using BIAcore surface plasmon resonance. The c18/A2 mAb was immobilized on a CM5 chip using standard amine coupling procedure. An LMP-1 antibody (Kindly provided by Dr Paul MacAry at the National University of Singapore) was used as a control. The purified c18/A2 monomer was subsequently injected in different concentrations at a flow rate of 20 μl/min. As shown in FIG. 3, the results confirmed that c18/A2 mAb, but not the LMP-1 antibody, bound to the c18/A2 monomer. Binding to c18/A2 mAb occurred with on- and off-rates of $1.1 \times 10^5 \, M^{-1} \cdot S^{-1}$ and $2.5 \times 10^{-3} M^{-1} \cdot S^{-1}$ respectively, resulting in the affinity ($K_D$) of 22.6 nM.

Recognition of C18/A2 Complexes Formed by Intracellular Processing

Figure 4:
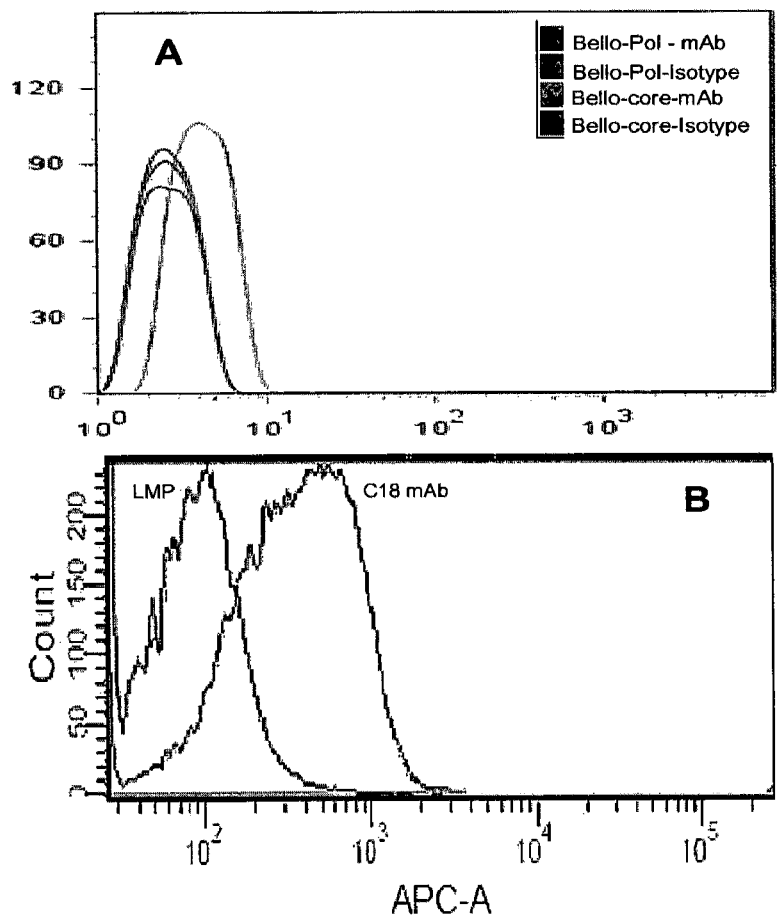
FIG. 4 are the results of the recognition of c18/A2 complexes produced by intracellular processing. (A) EBVB-core cells (constitutively expressing transfected core protein of HBV), EBV-pol cells (control) or DMSO (isotype control) were used. Significant staining above EBVB-pol cells or isotype controls was seen with EBVB-core cells. (B) IFN-γ treated HBV-expressing HepG2-117 cells were used. Significant staining with c18/A2 mAb was observed with HepG2-117 cells. These results confirm that C18/A2 complexes produced by intracellular processing were recognized by c18/A2 mAb.

To examine the ability of c18/A2 mAb to recognize peptide-MHC complexes produced by physiological processing, EBVB-core cells (A202) (kindly provided by F. Chisari, of The Scripps Research Institute) that constitutively express the transfected core protein of HBV were used. As a control EBVB-pol cells (kindly provided by F. Chisari, of The Scripps Research Institute) that express the polymerase of HBV were used. Significant staining above EBVB-pol cell or isotype controls could be seen with EBVB-core cells as shown in FIG. 4A.

HLA-A2 positive HepG2-117 cells (kindly provide by M. Nassal, University of Freiburg, Germany) that were stably transfected with whole HBV genome were used to detect the c18/A2 complexes on cells that produced HBV. These HepG2-117 cells produced HBV upon removal of Doxocycline from the culture. Treatment of these cells with 1% DMSO and 100 units/ml IFN-γ increased viral and MHC production, respectively. The HepG2-117 cells were incubated with 1 mg of c18/A2 mAb for 1 hr, washed and further incubated with anti-mouse IgG-APC antibodies (Invitrogen, USA) for 30 min. After washing 3 times, the cells were acquired on flow cytometer and level of fluorescent intensity analyzed with a Flow-Jo® software. As shown in FIG. 4B, significant staining with c18/A2 mAb was observed with HepG2-117 cells. An LMP-1 antibody (Kindly provided by Dr Paul MacAry at the National University of Singapore) which was used as a control did not stain these HepG2-117 cells. Taken together these results indicate that the TCR-like c18/A2 mAb was capable of detecting specific complexes formed after active and naturally occurring endogenous intracellular processing.

Detection of c18/A2 Complexes by Immunocytochemistry

Figure 5:
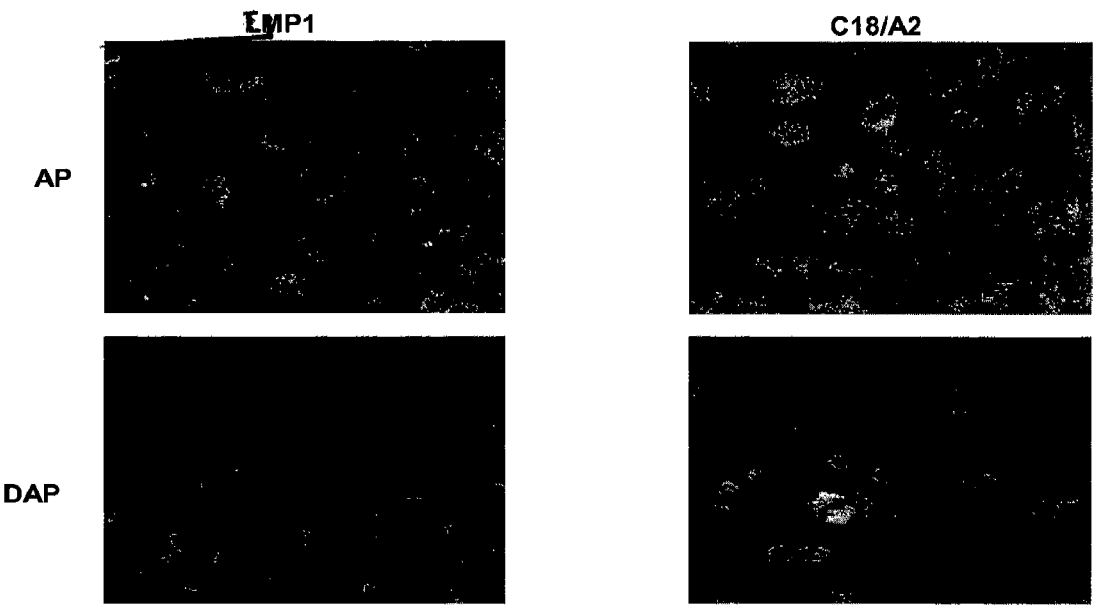
FIG. 5 are the results of the immunocytochemical staining of c18-27-MHC complexes. The c18/A2 mAb was able to recognize c18/A2 complexes that were presented by natural intracellular processing of the core antigen HBc18-27.

Another major potential application of TCR-like antibody is the direct in situ visualization of ligand containing cells within undisturbed tissues using immunocytochemical methods. In order to determine whether the c18/A2 mAb could be used for such studies, its ability to detect c18/A2 complexes on virus-producing HepG2 cells (HepG2-117) (kindly provide by M. Nassal, University of Freiburg, Germany) was tested. HBV expressing HepG2 cells (HepG2-117) were fixed in 1% paraformaldehyde permeablized with 0.5% saponin for 15 min at room temperature, washed and incubated with c18/A2 mAb, or a control LMP-1 antibody (Kindly provided by Dr Paul MacAry at the National University of Singapore). This was washed and a Tyramide Signal Amplification kit (Invitrogen, USA) was used to detect the binding. Nuclei were stained with DAPI. As shown in FIG. 5, positive staining could be observed with c18/A2 mAb and the staining was negative with isotype control or with the control LMP-1 antibody. These results demonstrated that c18/A2 mAb could be used to visualize the c18/A2 complexes on infected cells that were presented by natural intracellular processing of the core antigen.

Ability of c18-A2 mAb to Recognize Mutant c18-27 Peptides

During HBV infection the emergence of viral mutations within CTL epitopes, which contributes to viral persistence, has been reported. Substitutions in the CTL epitopes are poorly tolerated and might cause substantial decrease in activation of CTLs, suggesting that the emergence of a mutation in the epitope could allow virus escape.

Figure 6:
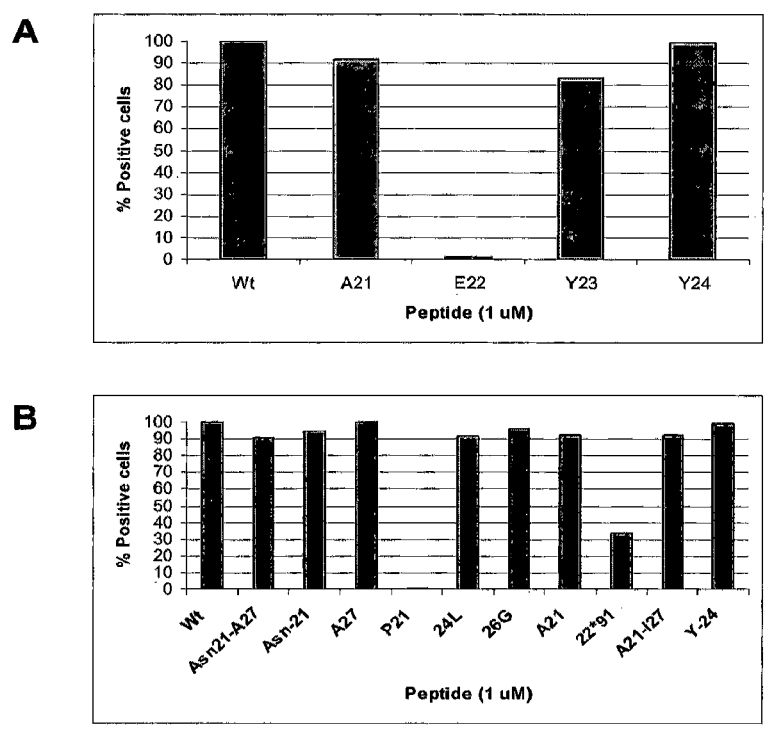
FIG. 6 is a graph showing the ability of c18/A2 mAb to recognize naturally occurring HBc18-27 mutants which have escaped CTL recognition. With the exception of E22 and P21, c18/A2 mAb was able to recognize several mutant peptides that failed to be recognized by CTL.

Natural amino acid substitutions within the core molecule of HBV that can affect CTL function have been reported. In order to verify if c18/A2 mAb can recognize naturally occurring mutant peptides that are able to inhibit CTL recognition, T2 cells obtained from ATCC were pulsed with 1 μM of wild-type c18-27 of SEQ ID NO:3 or naturally occurring mutant peptides and stained with c18/A2 mAb and flow cytometry was carried out. A list of the mutants is provided in Table 2. As shown in FIG. 6, c18/A2 mAb could recognize several natural mutant peptides that were shown to inhibit CTL activation. However, the recognition capacity of mAb was significantly decreased when cells were incubated with E22 and P21 mutant peptides. These results demonstrate that c18/A2 mAb can recognize several naturally occurring mutant peptides that were failed to be recognized by the c18/A2-specific CTLs.

TABLE 2

Amino acid Sequences of c18-27mAb light and heavy chain and naturally occurring HBc18-27 epitope mutant peptides.

| Name | Sequence | SEQ ID NO: |
|---|---|---|
| Amino acid sequence of variable domain of c18/A2 mAb Light Chain | DIQMTQSPASLSTSVGETVTITCRASGNIHNYLA WYQQKQGKSPQLLVYNAKTLADGVPSRFSGSG SGTQFSLKINSLQPEDFGSYYCQHFWSTPFTFG SGTKLEIK | 1 |
| Amino acid sequence of variable domain of c18/A2 mAb Heavy Chain | QVQLQQSGPELVKPGASVKISCKASGHTFTSYD INWVKQRPGQGLEWIGWIYPGDGSTKYNEKFK GKATLTADKSSSTAYMQLSSLTSENSAVYFCAR RDYGYSYAMDYWGQGTSVTVSS | 2 |
| HBc18-27 peptide (HBV genotype A/D/E/F) (WT C18-27) | FLPSDFFPSV | 3 |
| HBc18-27 peptide (HBV genotype B/C) (27I) | FLPSDFFPSI | 4 |
| A21 | FLPADFFPSV | 5 |
| Y23 | FLPSDYFPSV | 6 |
| Y24 | FLPSDFYPSV | 7 |
| Asn21-A27 | FLPNDFFPSA | 8 |
| Asn21 | FLPNDFFPSV | 9 |
| A27 | FLPSDFFPSA | 10 |
| P21 | FLPPDFFPSV | 11 |
| 24L | FLPSDFLPSV | 12 |
| 26G | FLPSDFFPGV | 13 |
| A21-I27 | FLPADFFPSI | 14 |

TABLE 2-continued

Amino acid Sequences of c18-27mAb light and heavy chain and naturally occurring HBc18-27 epitope mutant peptides.

| Name | Sequence | SEQ ID NO: |
|---|---|---|
| E22 | FLPS_E_FFPSV | 15 |
| 22Δ91 | FLPS_DTNMGL_ | 16 |

TABLE 3

Nucleotide Sequences of c18-27mAb light and heavy chain.

| Name | Sequence | SEQ ID NO: |
|---|---|---|
| Nucleotide sequence of variable domain of c18/A2 mAb Light Chain | gacatccagatgactcagtctccagcctccctatctacatctgtggg agaaactgtcaccatcacatgtcgagcaagtgggaatattcacaat tatttagcatggtatcagcagaaacagggaaaatctcctcagctcct ggtctataatgcaaaaaccttagcagatggtgtgccatcaaggttca gtggcagtggatcaggaacacaatttttctctcaagatcaacagcct gcagcctgaagattttgggagttattactgtcaacattttttggagtact ccattcacgttcggctcggggacaaagttggaaataaaa | 30 |
| Nucleotide sequence of variable domain of c18/A2 mAb Heavy Chain | caggttcagctgcagcagtctggacctgagctggtgaagcctggg gcttcagtgaagatatcctgcaaggcttctggtcacaccttcacaag ctacgatataaactgggtgaagcagaggcctggacagggacttg agtggattggatggatttatcctggagatggaagtactaagtacaat gagaaattcaagggcaaggccacactgactgcagacaaatcctc cagcacagcctacatgcagctcagcagcctgacttctgagaactct gcagtctatttctgtgcaagaagggactacggctactcttatgctatg gactactggggtcaaggaacctcagtcaccgtctcctca | 31 |

Example 2

Production of Petide-HLA-A2 Complexes

Extracellular domain of heavy chain and the β2m were expressed as inclusion bodies in _E. coli_ and refolded in vitro in the presence of 5-10 fold excess of c18-27 or env183-91 peptide. After refolding, the peptide-HLA-A2 mixture was concentrated and properly folded complex was isolated from contaminants on ion-exchange and size exclusion column chromatography methods. This complex was designated as monomer.

Generation of TCR-Like Antibodies

BALB/c Mice were immunized at 2-week intervals for a total of four times by intraperitoneal injection of a solution containing 25 μg of purified monomer (c18/A2 monomer or E183/A2 monomer) and Friends complete adjuvant (primary dose) or Friends incomplete adjuvant (3 booster doses). A final booster dose in saline without adjuvant was performed by tail injection three days before fusion. One day before fusion, mouse peritoneal macrophages were collected from peritoneal cavity of BALB/c mice and seeded in 96-well plate at $2 \times 10^4$ cells/well. Splenocytes from boosted mice were fused by PEG1500 with NS1 myeloma cells at a ratio of 1:1 using standard technique. The resulting hybridoma cell mixture was suspended in HAT selection medium and seeded in 96-well plates in which peritoneal macrophages were already placed, and selected for 2 weeks. Supernatants from hybridoma-formed (growing) wells were collected and tested for appropriate mAb specificity by flow cytometry. T2 cells pulsed with 1 μM of HBV c18-27 peptide or influenza A Matrix peptide (M1 peptide) were incubated with 50 μl of hybridoma supernatants for 30 min at 4° C., washed and further incubated with anti-mouse IgG alexa-488 secondary antibodies (Invitrogen) for 30 min at room temperature, washed and analyzed on BD FACSCAN flow cytometer using cell quest software. Positive cultures were sub-cloned twice by limiting dilution and further expanded. Similar protocol was followed for generation of E183/A2 antibody.

Selection of TCR-Like Antibodies

Figure 7:
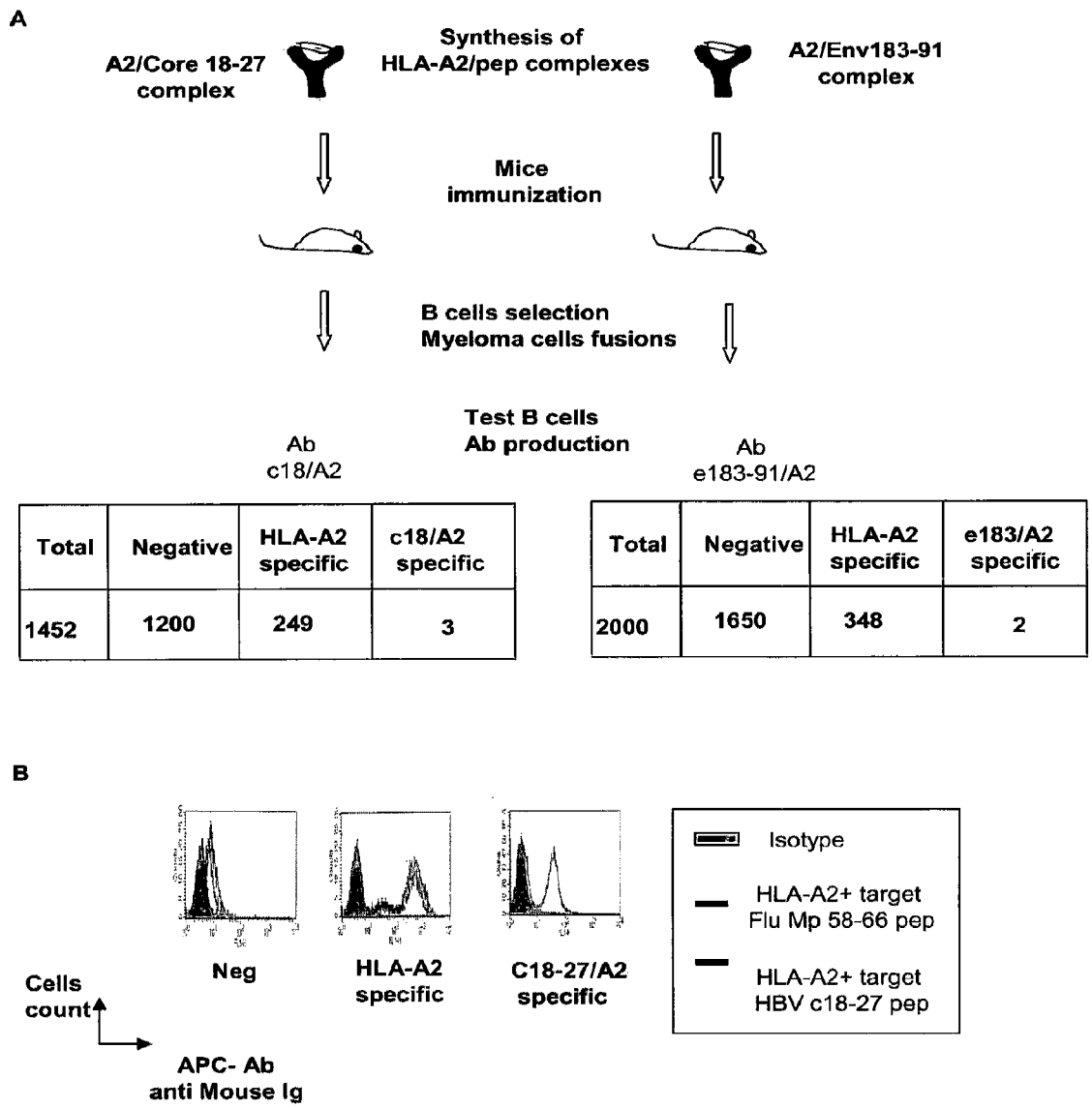
FIG. 7 is a schematic representation of the production of TCR-like antibodies. (A) Synthesis of HLA-A2 complexes, mice immunization, B cell selections and characterization of the specific antibody production as described in the Examples. The tables report the total number of screened hybridoma; (B) Histograms represent the different staining profile of B cell hybridoma supernatants. Stained cells are T2 cells pulsed with 1 μM each of Flu Mp58-66 or HBV c18-27 peptides. Cells were incubated with 50 μl of hybridoma supernatant or an irrelevant IgG1 mouse antibody, followed by washing and incubation with anti-mouse IgG-AF488 for 30 min. Cells were washed and analyzed on flow cytometry. Three different profiles (negative, specific for HLA-A2 molecules and specific for the core 18-27/HLA-A2 complex (c18/A2) are represented.

Antibodies able to recognize the HBV peptides/A201 complexes were produced by immunization of BALB/c mice with purified complex formed by HBV c18-27 or env183-191 peptide associated with the HLA-A0201 and β2-microglobulin (FIG. 7A). The correct folding of the pMHC and its stability was monitored with the conformation-specific HLA-A2 mAb, w6/32 which recognizes the HLA-A2 complex only when folded correctly. A single band was visible on the western blot with w6/32 antibodies, confirming the formation of properly folded monomer (data not shown). Splenocytes from immunized animals were fused with NS1 myeloma cells in 1:1 ratio and supernatants of the resulting hybridomas (~2000) were screened using HLA-A201+ T2 cells pulsed with an irrelevant HLA-A201-binding M1 peptide (Influenza A Matrix peptide 58-66, GILGFVFTL) or with the HBV core 18-27 peptide (FLPSDFFPSV) or with the HBVe183-91 peptide (FLLTRILTI, SEQ ID NO:34). The schematic representation of the selection process is shown in FIG. 7A. The binding of the antibody present in the supernatant to the peptide pulsed cells was detected using a secondary APC-conjugated goat anti-mouse IG antibody and the cells were analyzed by flow-cytometry. Three hybridomas produced antibodies (defined as c18/A2 Ab) which recognized T2 cells pulsed with HBVc18-27 peptide but not M1 peptide (FIG. 7B). Similarly, two hybridomas derived from mice immunized with HBVenv183-91/A2 complex produced antibodies (defined as E183/A2) that recognized only HBVenv183-91 pulsed T2 cells (not shown). These B cell hybridoma clones were stably expanded and the culture supernatants from one clone specific for each HBV peptide were collected in bulk, and antibodies were purified by Protein G Agarose column (data not shown). Thus repetitive immunization of mice with HBV peptide-MHC complexes was able to produce antibodies with TCR-like specificity.

Cell Lines

T2 cells were cultured in RPMI 1640 supplemented with 10% Fetal Bovine Serum, 20 mM HEPES, 0.5 mM sodium pyruvate, MEM and MEM non essential amino acids, Glutamex, 5 µg/ml Plasmocin (InvivoGen), 100 U/ml penicillin and 100 µg/ml streptomycin. HBV expressing HepG2 (HepG2-117) and vector control parent cell line (HepG2 TA2-7) cells were cultured in the Dulbecco's modified Eagle's medium (DMEM) supplemented with 10% tetracycline-free FBS (BD Biosciences, San Diego, Calif.), 20 mM HEPES, 0.5 mM sodium pyruvate, 100 U/ml penicillin, 100 µg/ml streptomycin, MeM nonessential amino acids (Invitrogen Ltd., Paisley, United Kingdom), 200 µg/ml G418 sulfate, 80 µg/ml Hygromycin B (AutogenBioclear, Wiltshire, United Kingdom). Doxocycline was added to medium at 1 µg/ml to suppress the HBV expression. HEK293 cells and NS1 myeloma cells were grown in DMEM supplemented with 10% FBS.

Characterization of TCR-Like Antibodies

Figure 8:
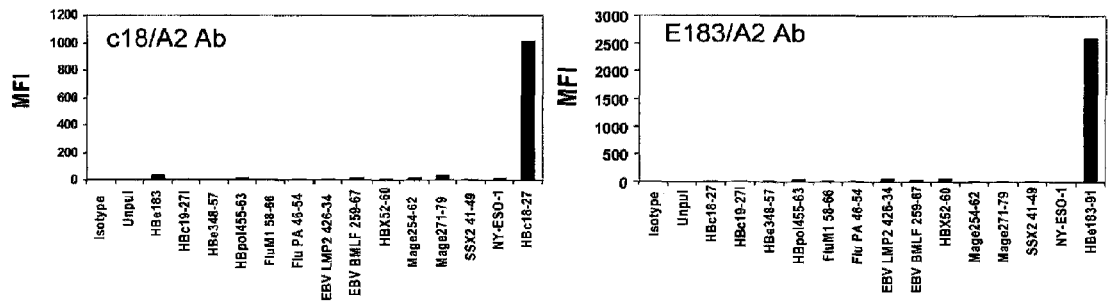
FIG. 8 is the results of the characterization of TCR-like antibodies. (A) Specificity of selected TCR-like antibodies was evaluated by incubating T2 cells with 1 μM each of the indicated peptides for 1 hr, washed 3 times and stained with 0.5 μg of c18/A2 mAb or E183/A2 mAb and analyzed as above. The mean fluorescence intensity (MFI) was plotted; (B) TCR-like antibodies are not inhibited by circulating HBV antigens: c18/A2 Ab or e183/A2 Ab were pre-incubated with 100 μl of indicated sera and culture supernatants of HBV producing HepG2-117 cells. This pre-incubated mAb-sera mixture was used to stain c18-27 or E183-91 peptides loaded (1 μM) T2 cells. Cells were analyzed using flow cytometry and MFI was plotted. The recognition capacity of mAb was not inhibited by the circulating antigens of patient sera; (C) Binding characterization of the two TCR-like Ab. Titrated concentrations of the two TCR-like Ab were tested with peptide pulsed T2 cells. Bars represent the MFI values obtained at the indicated concentrations of TCR-like Abs.
Figure 8:
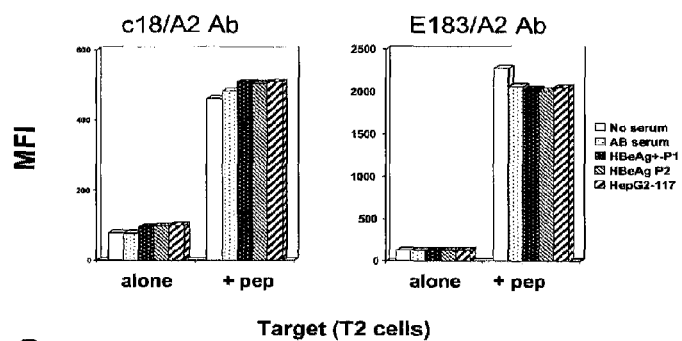
Figure 8:
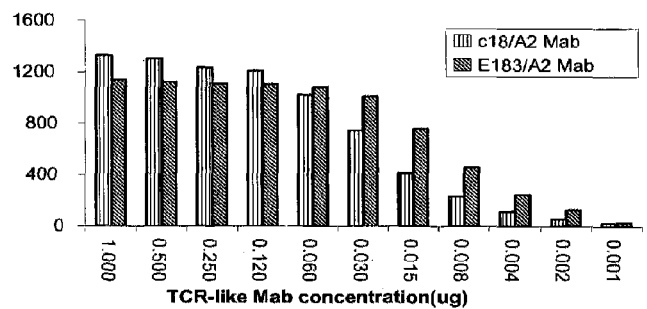

Although the initial hybridoma screening already showed the specificity of TCR-like antibodies to their cognate ligands, a series of assays were performed to exclude cross-reactivity with other HLA-A201/peptide complexes. T2 cells were incubated with a variety of HLA-A201 binding peptides derived from HBV polymerase, X and envelope proteins as well as peptides derived from EBV, flu, CMV and a wide variety of tumour associated antigen epitopes as mentioned in Materials and Methods (Table. 4). FIG. 8A showed that both c18/A2 and E183/A2 TCR-like mAb reacted specifically only with target cells pulsed with the respective peptide.

TABLE 4

Peptides used in characterisation of TCR-like antibodies

| Peptide | Sequence | SEQ ID NO: |
|---|---|---|
| HBc18-27 | FLPSDFFPSV | 3 |
| HBe183-91 | FLLTRILTI | 24 |
| HBc19-27I | LPSDFFPSI | 34 |
| HBe348-57 | GLSPTVWLSV | 25 |
| HBpol455-63 | GLSRYVARL | 21 |
| Flu M1-58-66 | GILGFVFTL | 17 |
| Flu PA46-54 | FMYSDFHFI | 29 |
| EBV LMP2 426-34 | CLGGLLTMV | 28 |
| EBV BMLF 259-67 | GLCTLVAML | 27 |
| HBX52-60 | HLSLRGLPV | 18 |
| Mage 254-62 | GLYDGMEHL | 19 |
| Mage3-271-79 | FLWGPRALV | 22 |
| SSX 2 (41-49) | KASEKIFYV | 20 |
| NY-ESO-1 (157-65) | SLLMWITQA | 23 |

Since patients with chronic hepatitis B present high levels of circulating soluble HBsAg and HBeAg, we also investigated whether HBV circulating antigens might interfere with the recognition of pMHC complexes. This was tested by incubating HBeAg or HBsAg positive sera collected from HBV chronic patients and culture supernatant from HBV producing HepG2-117 with TCR-like antibodies for 1 hr. The resulting mixture was used to stain cells expressing respective pMHC complexes. FIG. 8B showed that the binding capacity of the TCR-like antibodies was not altered by the HBV circulating antigens or other sera components.

The pre-incubation of the two TCR-like mAbs with their cognate peptides alone (c18-27 and e183-91 peptides—1 uM) did not result in the decreased staining of the specific target (not shown).

To define the concentrations required for optimal staining both c18/A2 and e183/A2 Abs were titrated over a range of 1 µg to 0.001 µg/ml concentrations and then used to stain T2 cells pulsed with 1 µM of HBV core 18-27 or HBV env 183-91 peptides (FIG. 8C). The specific MFI values of the antibodies staining was obtained by subtracting the mean fluorescent values of non peptide pulsed T2 cells (control) from the MFI obtained in peptide-pulsed T2. The staining reactions saturates at 0.5 µg/ml with c18/A2 Ab and at 0.06 µg/ml with e183/A2 Ab. Both antibodies shows the ability to distinguish peptide pulsed from non-peptide pulsed cells at working concentrations of 0.004-0002 µg/ml even though the level of staining was low (MFI=~200 c18/A2 Ab; MFI=~300 with e183/A2 Ab). The MFI values obtained with e183/A2 Ab were higher than the one obtained with c18/A2 Ab over the whole range of concentrations tested, suggesting than e183/A2 Ab has a better affinity to its specific pMHC complex than the c18/A2 Ab. Since saturated staining was obtained for both antibodies at 0.5 µg/ml this concentration was used in the following experiments unless differently indicated.

Detection of pMHC Complexes on Target Cells with Flow Cytometry

T2 is a mutant cell line that lacks transporter-associated antigen processing (TAP) 1 and 2 which allows efficient loading of peptides. HepG2 cells are an HLA-A2+ hepatoma line. The peptide pulsed T2 cells, peptide pulsed or HBV transfected HepG2 cells were incubated with 0.5 µg of c18/A2 or E183/A2 mAb in 50 µl FACS staining buffer (1% BSA in PBS with 0.01% sodium azide) per tube for 1 hr at 4° C. The cells were washed thrice, incubated with 1 µg of anti mouse-IgG secondary antibody tagged with appropriate fluorophore in 50 µl staining buffer. After a further washing cells were analyzed by BD FACSCanto flow cytometer. Where appropriate, the histograms were overlaid using Flowjo Software.

Degeneracy of TCR-Like Antibody Recognition.

The ability of the TCR-like mAbs to tolerate amino acid (AA) substitution within the viral peptides presented by HLA-A201 molecules was tested. The recognition pattern of the TCR-like antibodies was compared with the one of CD8 T cells specific for the same epitopes. These experiments could clarify the possible different nature of the recognition between the TCR-like mAb and CD8 T cells and directly test the ability of TCR-like mAb to recognize different HBV genotypes or HBV quasi-species with mutations within the targeted HBV epitopes.

Figure 9:
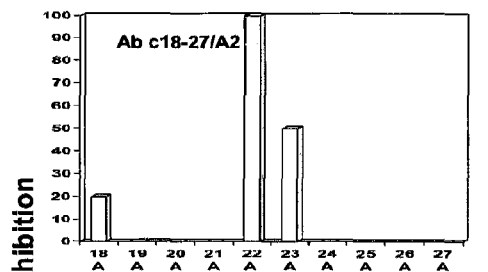
FIG. 9 is graphs showing the results of fine mapping of the TCR-like Ab specificity. (A) Influence of AA mutations within core 18-27 and env 183-91 epitope on TCR-like Ab and CD8 T cell recognition is shown. T2 cells were pulsed with 1 μM of core 18-27 or env 183-91 peptides with or without (wt) alanine substitutions at the indicated positions. Inhibition of TCR-like Ab binding (upper quadrants) and CD8 T cell activation (lower quadrants) elicited by Alanine substitutions on the WT core 18-27 (Left quadrants) and env 183-91 (right quadrants) peptides are indicated by bars. % of inhibition is calculated with the following formula: MFI (or CD 107 expression) values obtained with Alanine substituted peptides divided by values obtained with WT peptides×100; (B) The c18/A2 Ab recognition of naturally occurring core 18-27 mutants. T2 cells were pulsed with 1 μM of wt c18-27 or amino acid substituted peptides followed by staining with c18/A2 Ab. Bars represent the MFI values obtained by flow cytometry analysis; (C) E183/A2 Ab is exclusively specific for env183-91 peptide of HBV gen A/C/D. T2 cells were pulsed with 1 μM env 183-91 peptides with the indicated substitution at position 187. 187 R is characteristic of HBV gen A/C/D isolates, K 187 of HBV genotype B/E/F.
Figure 9:
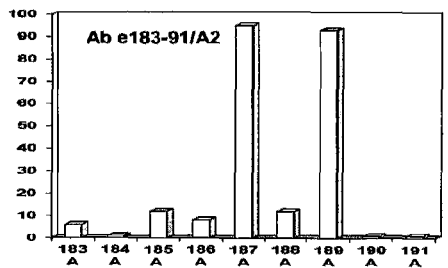
Figure 9:
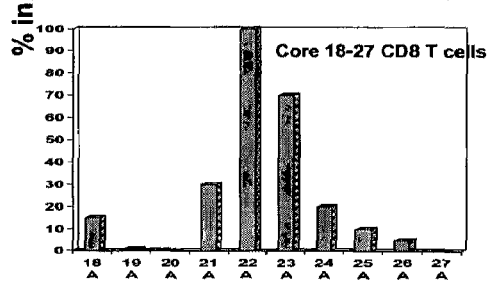
Figure 9:
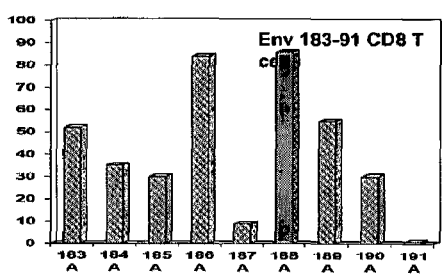
Figure 9:
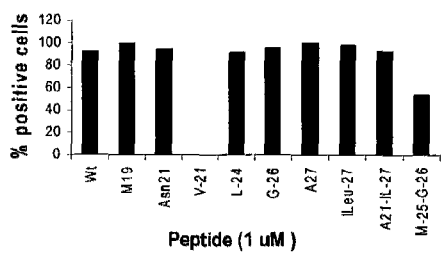
Figure 9:
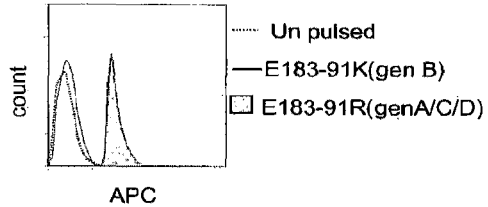

The ability of core 18-27 specific CD8 T cells and mAb to recognize the AA substituted core 18-27 peptides was tested. FIGS. 9A and B showed that AA substitutions at position 22 and 23 were not tolerated by both CD8 T cells and c18-27/A2 mAb. Such data was consistent with previous functional CD8 T cell recognition results and with crystallographic data related to the core 18-27/HLA-A201 complex. AA at position 22 and 23 bulge out from the HLA-class I grove and are therefore structurally positioned to have a major impact on the interaction between the HBV-viral peptide/A2 complex and their receptors. Similar analysis was performed for target recognition e183/A2-specific antibody and CD8 T cells. E183/A2 specific CD8 T cell clones were produced and tested in parallel with the E183/A2 specific mAb against target cells pulsed with single AA substituted env 183-91 peptides. Amino acid substitutions at position 187 and 189 were not tolerated by e183/A2 Ab (FIG. 8C), whereas 186 and 188 were required for TCR binding (FIG. 9), indicating the different way of recognition by antibody and CD8+T cell specific for E183/A2.

Whether natural AA substitutions present in distinct HBV viral isolates can inhibit TCR-like mAb recognition was tested. These natural AA substitutions within the core 18-27 epitope has been shown to alter the core 18-27 specific CD8 T cell response. FIG. 8A showed that the c18/A2 mAb can tolerate, with the exception of V-21 substitution, several mutations including M-19, Asn-21, L-24, Y-24, G-26, ILeu-27, A-27, M-25G-26 and A-21-I-27 (FIG. 9B). Importantly, core 18-27 peptide with Isoleucine to Valine substitution at position 27, which represent the core 18-27 sequence characteristic in HBV genotype B, C and some F strains did not affect c18/A2 mAb recognition. This is in line with the fact that such mutation alters only the binding of the peptide to the HLA-A201 molecule but not his recognition. Thus, this data indicated that c18/A2 antibody can potentially recognize the six more HBV genotypes (A, B, C, D, E, and F) and several naturally occurring mutant peptides of core 18-27 epitope.

In contrast, the e183/A2 Ab was exclusively specific for the env183-91 epitope sequence of HBV genotypes A/C/D and not HBV genotype B, E, F. The Arg-187 classically found in HBV genotypes A/C/D is substituted to Lys-187 in genotype B, E, F. FIG. 9C shows that the e183/A2 antibody was not able to recognize the env183-191(K) in the context of HLA-A201, indicating the exclusive specificity of the antibody for the envelope proteins detected in the majority of HBV Genotypes A/C/D.

Degranulation Assays of HBV-Specific CD8 T Cells

CD107 PE antibody (BD Pharmigen, San Diego) was added to the wells at the beginning of the 5 hour incubation of CD8 T cells with target cells pulsed or unpulsed with different peptides. Following the incubation cells were washed, stained with Cy-chrome-conjugated anti-CD8 (BD Pharmingen, San Diego, Calif.), washed and analyzed by flow cytometry.

Sensitivity of TCR-Like mAb.

Figure 10:
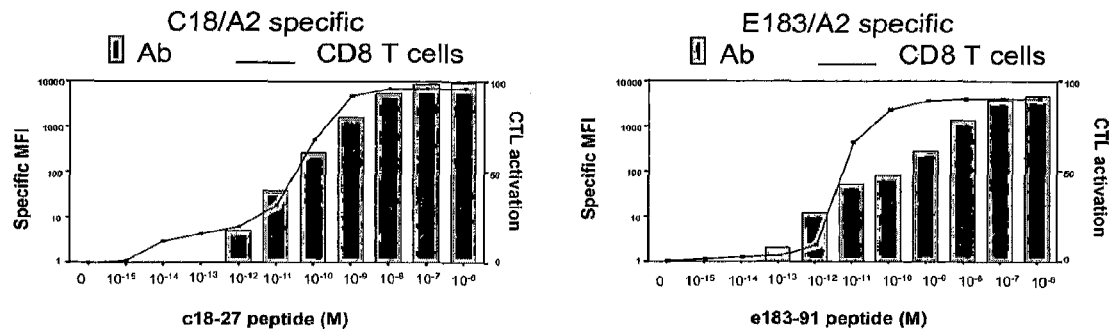
FIG. 10 are graphs showing that TCR-like antibodies detect pMHC complexes with a sensitivity similar to HBV-specific CD8 T cells. T2 cells were incubated with indicated concentrations of c18-27 or E183-91 peptide for 1 hr and used in the binding of respective antibody (Bars)- or CD8 T cell activation (Line). Binding of antibody was detected by flow cytometric analysis. CD8 T cell activation was calculated by the % of CD107 expressing CD8 T cells after 5 hours incubation with target cells. Experiments were done in parallel and replicated. Symbol represents the mean value of two experiments.

Whether the recognition of pMHC complexes by the two TCR-like mAbs approached the sensitivity of CD8 T cells specific for the same pMHC complex was analysed. T2 cells were pulsed with the indicated concentrations of synthetic peptides, washed and then stained with the two TCR-like Abs. FIG. 10 (Bars) showed that the c18/A2 mAb and env183/A2 MAb staining intensity was proportional to the peptide concentrations used for pulsing T2 cells and that $10^{-12}$ M (1 pM—FIG. 8A) of core 18-27 and $10^{-13}$ M (100 fM—FIG. 8B) of env 183-91 peptides were sufficient to detect specific binding.

The ability of TCR-like MAb to detect complexes on the surface of infected cells with the one of CD8 T cells of identical specificity was then compared. Core 18-27 specific and env 183-91 specific CD8 T cells were challenged against T2 cells pulsed with the different specific peptide concentrations used for antibody detection staining and the activation of CD8 T cells was quantify by measuring the expression of CD107 (degranulation) on CD8 T cells. The frequency of CD8 T cells specifically activated by peptide pulsed T2 cells was superimposed to the data relative of TCR-like Ab detection ability (FIG. 10). The data showed that the core 18-27 specific CD8 T cells were activated at peptide concentrations lower to the ones necessary to detect c18/A2 Ab specific staining of peptide pulsed T2 (10-100 fM versus 1 pM—FIG. 10). In contrast, the env 183-91 specific CD8 cells required target cells pulsed with peptide concentrations higher than the ones necessary to detect env 183/A2 Ab mediated T2 staining (10 pM versus 100 fM). The two TCR-like antibodies can detect cells pulsed with peptides at low pM range and their sensitivity is, at least for the env 183-91/A2 specific antibody superior to the one of CD8 T cells specific for the same complex.

Lentiviral Transduction of HepG2 Cells $4 \times 10^6$ HEK293 cells were plated in 10 cm tissue culture plates and were co-transfected using $CaCl_2$ with pLVX-HBc or pLVX-HBs and packaging vectors provided in the Lenti HT packaging mix (BD Clontech). 24-48 hr after transfection, the vector supernatants were collected and clarified. HepG2 cells were transduced with vector supernatants in the presence of 7 µg/ml polybrene for 24 hr. Cells were selected for 2 days in 7 µg/ml puromycin and then analyzed by flow cytometry following staining with c18/A2 mAb or E183/A2 mAb.

Visualization of pMHC Complexes

HepG2 and HepG2-117 cells were cultured on cover slips in DMEM medium with 1% DMSO. Doxocyclin was removed from the medium to allow the production of HBV. Cells were treated with 1000 U/ml IFN-γ for 2 days before staining with antibodies. Cover slips were washed with PBS for 3 times and fixed in freshly prepared 1% paraformaldehyde for 15 min at room temperature. After washing thrice with PBS, cover slips were blocked with 5% goat sera for 1 hr followed by incubation with 1 µg of c18/A2 or E183/A2 antibody overnight at 4° C. Cover slips were washed in PBS+ 0.05% tween 20 (PBST) 3 times. Alexa Fluor 647-Tyramide Signal Amplification kit (Invitrogen) was used to reveal the primary antibody binding with the exception that goat anti mouse IgG-HRP polymer (DAKO) was used instead of anti mouse IgG-HRP provided in the kit. The rest of the protocol was same as recommended by the manufacturer. Cover slips were mounted in antifade gold reagent containing DAPI (Invitrogen), and images were obtained by Carl Zeiss LSM 510 META upright confocal microscope.

Ability of TCR-Like Antibody to Recognize HBV Infected Cells.

To test if the TCR-like antibodies directly in patient's samples required a robust demonstration that such antibodies can directly recognize HBV infected hepatocytes. The ability of TCR-like Ab to recognize T2 cells pulsed with peptide concentrations at pM range and with a recognition level similar to the one of HBV-specific CTL was encouraging but hepatocytes constitutively express low levels of HLA-class I molecules. Furthermore, their antigen processing machinery was extremely inefficient in the generation of peptide/HLA-class I complexes, thus the quantity of the TCR-specific ligands expressed by HBV infected hepatocytes can be much lower than the level in HBV peptide pulsed T2 target cells.

The capacity of TCR-like mAb to recognize pMHC complexes produced by physiologically active intracellularly processed peptide in the context of HLA-A2 was first evaluated by flow cytometry analysis. For this purpose, we performed lentiviral-mediated transduction of HepG2 cells (which are HLA-A201+) with pLVX-HBcAg or pLVX-HBsAg plasmids expressing full length HBcAg or HBsAg proteins, respectively. Significant staining with c18/A2 and E183/A2 antibodies above empty vector transduced cells could be clearly seen (FIGS. 11A and B), demonstrating that these antibodies can recognize pMHC complexes endogenously produced in hepatocytes.

Whether hepatoma cell lines (HepG2) stably transfected with a tetracycline (Tet) responsive promoter-controlled HBV genome can be stained by the two TCR-like Abs was then tested. This Tet-controllable HBV transfected HepG2 line (HepG2-117) produced different quantity of HBV virions and HBcAg antigens after removal of doxycycline (Dox), while HBsAg production is regulated by internal promoters and thus his expression is largely unaffected by Dox. In addition, DMSO treatment of HepG2-117 dramatically increases the total number of HBV-DNA×cell and thus allow us to study the level of HBV pMHC expression over a wide range of HBV production.

A minimal level of staining with the c18-27/A2 Ab on HepG2-117 cells six days after removal of Dox was observed in comparison with the staining level observed on HepG2 cells transfected with empty vector (HepG2-control) and on HepG2-117 culture in the presence of Dox. Only treatment of HepG2-117 with DMSO (which increases HBV-DNA content) and IFN-gamma (increases Ag-processing/presentation ability of hepatocytes) results in a clear staining with c18/A2 Ab of all cells.

Specific staining of HepG2-117 with E183/A2 Ab was observed in comparison with the staining detected on HepG2 transfected with empty vector (HepG2-control). However, In accordance with the fact that HBV envelope mRNAs are not fully subjected to Tet regulation, E183/A2 Ab staining of HepG2-117 treated or not treated with Dox was identical. E183/A2 Ab staining detect two populations of cells likely expressing different quantity of HBsAg. Treatment of HepG2-117 cells with DMSO and IFN-gamma dramatically increases the staining level with e183/A2 Ab.

Figure 11:
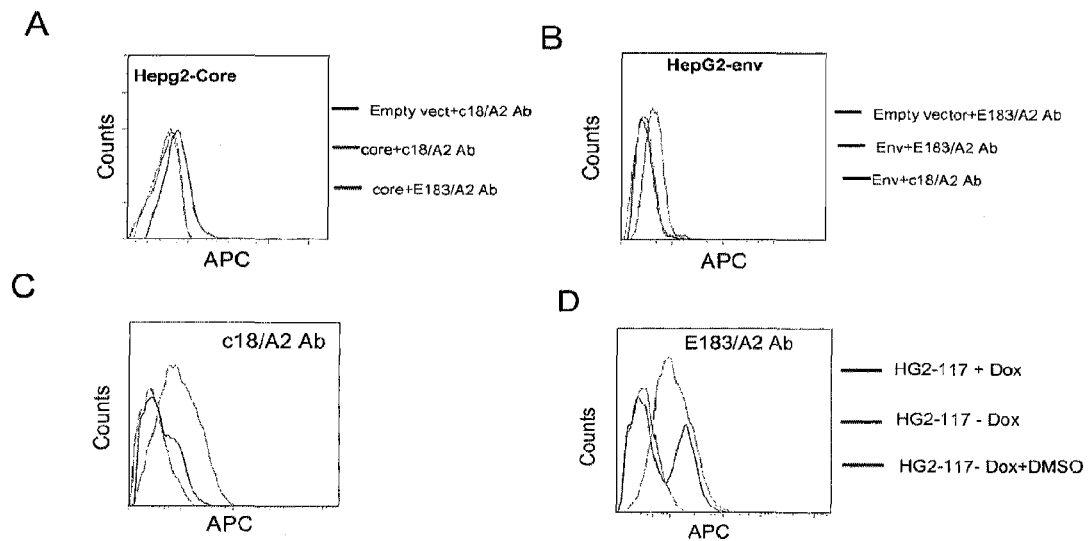
FIG. 11 illustrates the detection of pMHC complexes produced by intracellular processing: HepG2 cells were either HBcAg (A) or HBsAg (B) transduced with lentiviral vectors. Empty vector transduced cells were used as control. HepG2-117 cells were grown in the presence or absence of Doxocycline and stained with c18/A2 Ab (C) or e183/A2 Ab (D). (E) Visualization of pMHC complexes. HepG2-117 +Dox (no HBV) and −Dox (HBV) cells were fixed with 1'/oPFA, and stained with c18/A2 Ab and e183/A2 Ab. Alexa Fluor-647-Tyramide Signal Amplification kit was used to visualize the antibody binding (Red, shown as light grey in FIG. 11). Nuclei were stained with DAPI (Blue, shown as dark grey in FIG. 11).
Figure 11:
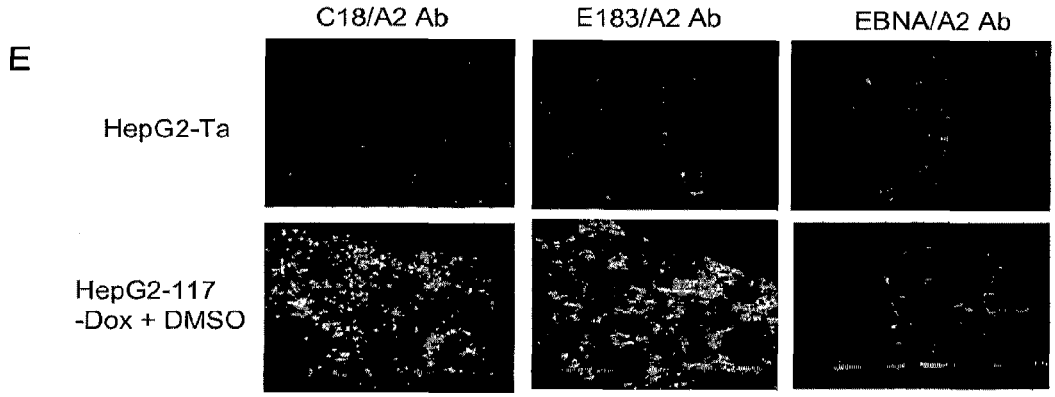

Thus the two TCR-like Abs were able to recognize hepatocyte-like cells the intracellular processing product of endogenously synthesized HBV antigens, expressed as a single protein (FIGS. 11A, B) or as a result of full HBV replication (FIGS. 11C and D).

The ability of the two TCR-like antibodies to recognize their corresponding pMHC (c18-27/A2 and E183/A2) on HBV producing hepatocytes-like cells was also confirmed using immunohistological methods. HepG2-117 cells cultured in Dox-media and DMSO treated were fixed in 1% paraformaldehyde for 15 min at room temperature, washed, and followed by incubation with c18/A2 or E183/A2 mAb. Tyramide Signal Amplification kit was used for visualization of antibody staining. As shown in FIG. 11E, recognition of pMHC could be seen with both antibodies and the staining was negative in non HBV-transfected HepG2 cells and with a control antibodies. Bright staining was obtained with E183/A2 antibody because of higher density of E183/A2 complexes on infected HepG2-117 cells. However, very faint/negative staining with c18/A2 and e183/A2 Ab was observed on HepG2-117 Dox-cells without DMSO (data not shown).

Figure 12:
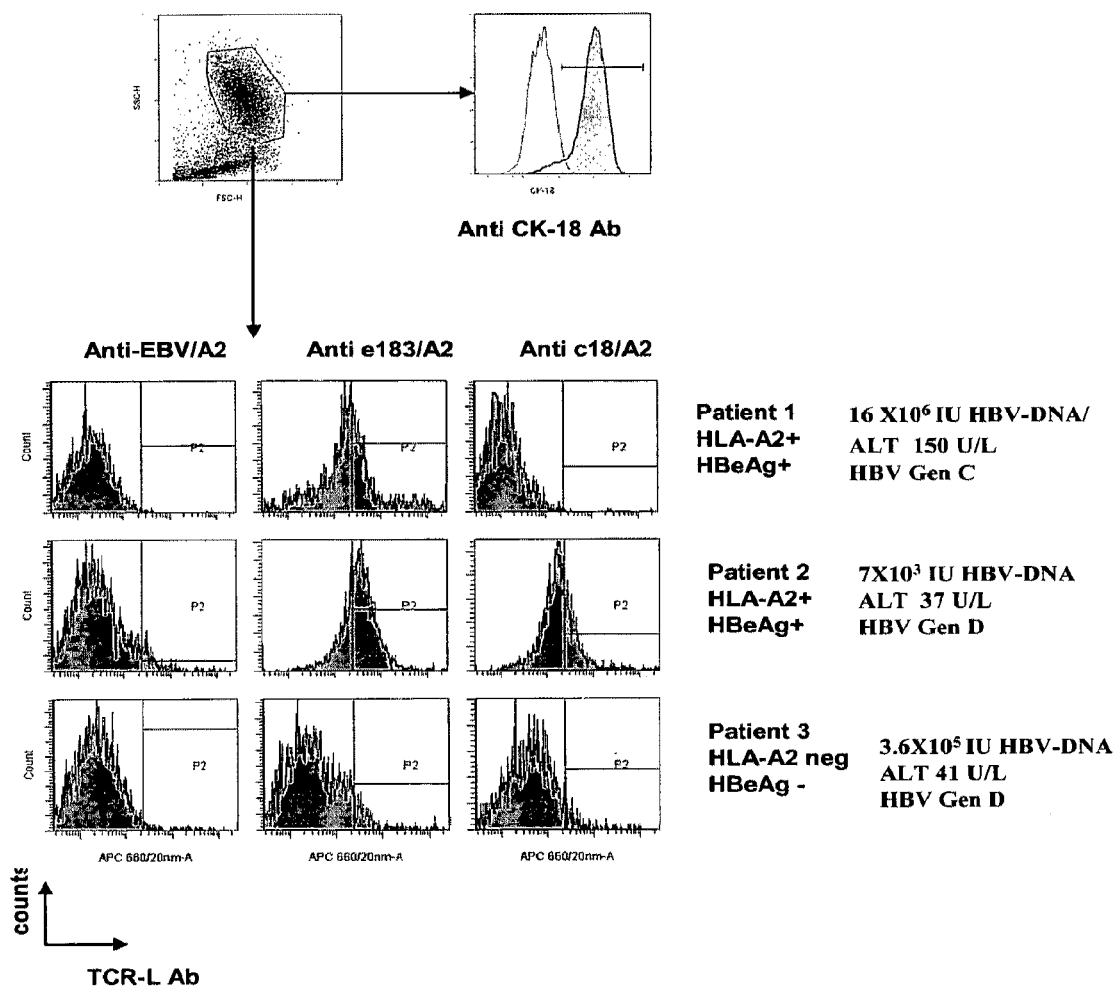
FIG. 12 illustrates the recognition of pMHC on cells purified from CHB liver biopsies. Dot plot shows forward and size scatter of suspended cells derived from liver biopsies of CHB patients. The expression of Ck-18 (a hepatocyte specific protein) on gated cells is shown in the histogram. More than 90% of cells with the indicated morphology are expressing Ck-18. For detection of the specific pMHC on cells derived form liver biopsies, mechanically processed cells were stained with the indicated TCR-like antibodies. HLA-A2 positivity and clinical/virological features of the distinct patients are indicated.

On average HepG2-117 cells expanded without Dox carried about 130 HBV-DNA copies×cell. Such quantity is compatible with the average quantity of HBV-DNA×cell detected on hepatocytes of HBeAg+ CHB patients (~100 copies×cell) Since specific TCR-like Abs staining of HepG2-117 with this level of HBV replication was achieved only with flow cytometry, biopsies of CHB patients were mechanically treated to reach individual cell suspension, stained with antibodies and immediately analyzed with flow cytometry (FIG. 12). CHB patients were first tested for HLA-A201 expression and biopsies of HLA-A2 negative subjects were used as a negative control and to test whether cells with a morphology compatible with hepatocytes (cells with elevated complexity and size-on forward and size scatter) were expressing cellular markers like Ck-18, which is an hepatocyte specific marker. Cells obtained from biopsies of HLA-A2+ were instead stained only with c18/A2 and E183/A2 Abs and with a control antibody specific for EBV M/A2 complex. The limited number of cells available from liver biopsies and the fact that secondary antibodies needs to be used for the staining has been the limiting factor that has so far precluded multiple staining of the cells obtained from liver biopsies. FIG. 12 shows that c18/A2 and e183/A2 Abs but not the control A2-EBV antibody were able to distinguish cells purified form liver biopsies of HLA-A201 positive CHB patients while no positive staining was detected in HLA-A2 negative patients. The A2+ patient infected with genotype C showed a positive staining only with e183/A2 Ab but not with c18/A2 Abs despite the level of HBV-DNA was superior to the one present in HBV Gen D patient 2, in whom both C18/A2 and e183/A2 Abs cells were able to specifically stain liver biopsy cells. It is likely that this diversity of staining is related to the better affinity of core 18-27 epitope of HBV gen D in comparison of HBV gen C. HBV gen D core 18-27 sequence has a Val at position 27, while core 18-27 of HBV gen C present an Isoleu at position 27. This latter mutation decreases the binding of core 18-27 epitope to the A2 molecule and thus the quantity of the specific pMHC A2/core 18-27 present in the surface of infected cells.

The high sensitivity of the HBV-specific TCR-like antibodies is confirmed by the fact that they are able to recognize pMHC complexes on the surface of target cells with an efficiency approaching (c18/A2 Ab) or even better (e183/A2 Ab) than the one of HBV-specific CD8 T cells. In particular, the e183/A2 specific Ab can specifically distinguish cells pulsed with env 183-91 peptide concentrations so low (100 fM) which are unable to activate env 183-91 specific CD8 T cells.

Quantification of pMHC

Figure 13:
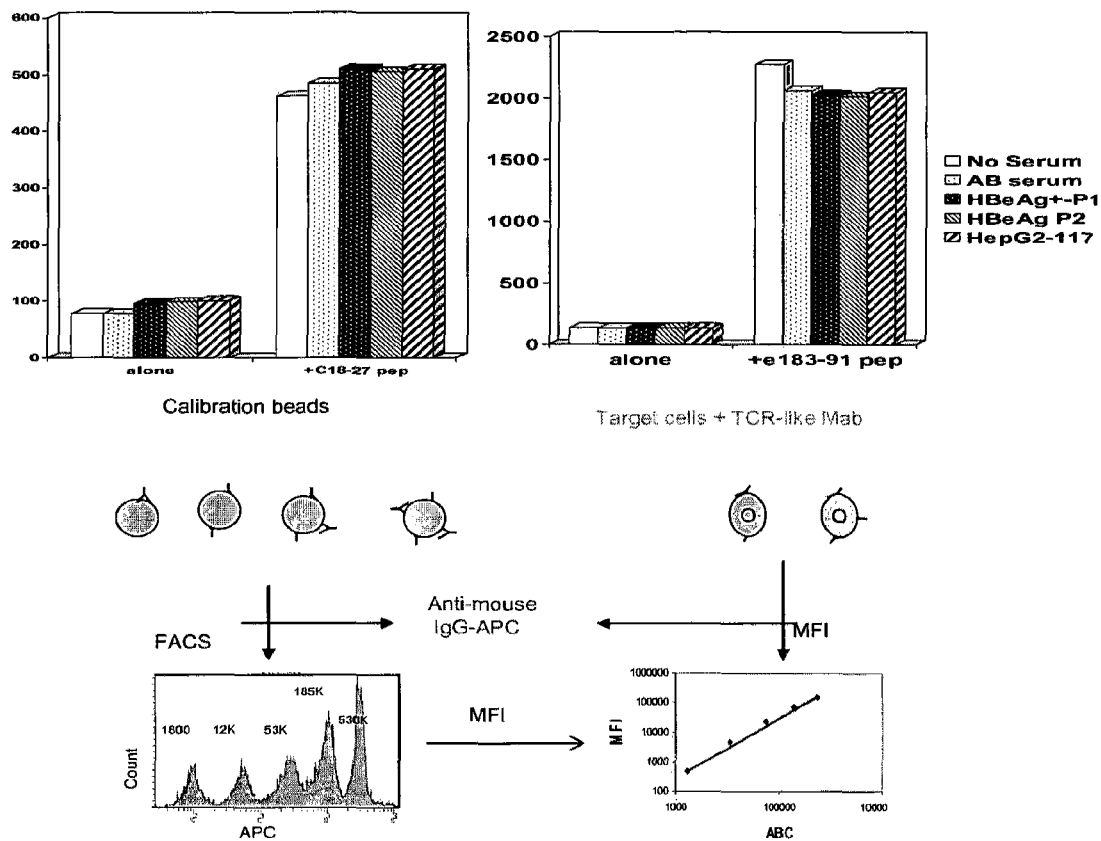
FIG. 13 is a graph of the results of quantitation of pMHC and CTL activation. To obtain the precise number of pMHC, the MFI of an aliquot of cells (incubated with concentration of c18-27 peptides and e183-191 peptides) interpolated on a calibration curve generated using calibration beads displaying known quantities of mouse IgG mAb.

The QIFIKIT (DAKO) was used to quantify the pMHC present on the surface of cells. The protocol used for the quantification was as recommended by the manufacturer. In brief, cells were incubated with 1 µg of c18/A2 or E183/A2 mAb in 50 µl of FACS staining buffer for 1 hr at 4° C. followed by washing for 3 times. In separate tubes, cells, Set-Up Beads, and Calibration Beads displaying different, but well-defined quantities of mouse IgG mAb molecules, in parallel, were incubated with anti-mouse IgG-APC secondary antibodies for 1 hr at 4° C. Cells were washed thrice and acquired on FACSCanto. The MFI of each population of the calibration beads was obtained and used to construct calibration curve. The MFI of cells was determined and their specific MFI was obtained by deducting the MFI of isotype control cells, and precise number of antigens (pMHC) was calculated by interpolation on the calibration curve (FIG. 13). Similar protocol was used to quantify pMHC from HBV producing HepG2 cells that were expressing pMHC after intracellular, endogenous processing.

Quantification of pMHC Complexes on HBV Producing HepG2-117 Cells.

TCR-like Abs were used to derive a relative quantification of the specific pMHC complexes displayed on individual infected cells. The number of pMHC complexes expressed in HBV producing HepG2-117 cells and the HLA-A2 occupancy rate of the envelope and core peptides on HBV producing cells were measured. The fluorescent intensity of the different cell lines (HepG2 117 −Dox, Hep G2 117 +Dox) stained with TCR-like Abs or anti HLA-A2 Ab was compared with the fluorescent intensities of calibration beads with know numbers of binding sites per bead (QuantiBRITE beads method—FIG. 13). Table 5 shows that HepG2-117 cells containing about 130HBV-DNA copies×cell express respectively 140 c18-27/A2 and 1020 e183-91/A2 complexes×cell. The occupancy rate of total HLA-A2 molecule was 0.036% and 0.26% respectively for c18-27 and env 183-91 epitopes.

TABLE 5

Quantization of HBV epitopes/A2 complexes on the surface of hepatocyte-like cells. The fluorescent intensity (MFI) of stained cells was compared with MFI of calibration beads with known numbers of ligands x beads as detailed in the material and methods. Relative estimation of HBV-DNA/cell is derived from the data of Sun et al.

| Cells | HBV-DNA/ cell | HLA-A2/cell | C18/A2 sites/cell | HLA-A2-Occupancy (%) | E183/A2 sites/cell | HLA-A2-Occupancy (%) |
|---|---|---|---|---|---|---|
| HG2-empty vector | 0 | $3.5 \times 10^5$ | 0 | 0 | 0 | 0 |
| HG2117 + Dox | 3-4 | $3.6 \times 10^5$ | 9 | 0.002 | 1024 | 0.28 |
| HG2117 − Dox | 134 | $4.0 \times 10^5$ | 144 | 0.036 | 1013 | 0.26 |

TABLE 6

Amino Acid sequences of HBe183-191mAb light and heavy chain.

| Name | Sequence | SEQ ID NO: |
|---|---|---|
| Amino Acid Sequence of variable domain of E183/A2 mAb Light chain | DIQMTQSPASLSASVGETVTITCRASENIYSYLA WYHQKQGKSPQLLVYIAKTLAEGVPSRFSGSG SGTQFSLKIDSLQPEDVGSYYCQHHYGTPYTF GGGTKLEIKR | 32 |
| Amino Acid Sequence of variable domain of E183/A2 mAb Heavy chain | QVQLQQPGAEFVKPGASVRLSCKASGYTFSSY WMHWVKQRPGQGLEWIGEIDPSDSYTNYNQK FKGKATLTVDKSSSTAYMQFSSLTSEDSAVYY CATSGYDVGVDYWGQGTTLTVSS | 33 |

The high sensitivity of the two TCR-like antibodies allows direct recognition of pMHC complexes on the surface at infected hepatocytes. Hepatocytes which express very low levels of HLA-class I molecules and have poor antigen processing ability can also be recognised as the antibodies of the present invention recognise pMHC ligand not only on HepG2 −HBV producing cells but also directly ex vivo in biopsies of CHB patients.

A comparative analysis of the number of envelope and core derived pMHC complexes on the surface of HBV infected cells indicated that the quantity of envelope-MHC complex exceeded the quantity of core-MHC complexes in HBV producing HepG2 cells and on hepatocytes of chronic HBV infected patients. This quantitative difference is likely dependent on the superior synthetic production of HBsAg in comparison to HBcAg/HBeAg. Such results could suggest that HBV envelope is a better target than HBV core for HBV-specific CD8 T cell mediated control. Interestingly, this quantitative hierarchy of TCR-ligands expressed on cell surface collides with the immunodominant hierarchy of HBV-specific CD8 T cell frequency in HBV infected patients.

Despite being present in most of the HLA-A201+ acute HBV patients, E183/A2 specific CD8 T cells are often detected at frequency lower than c18/A2 specific CD8 T cells. The discrepancy of such results is an indication of the potential of the TCR-like antibodies for in depth studies of HBV pathogenesis.

By performing experiments of pMHC detection with immunohistochemical staining on fixed biopsies and HepG2 117, we noted that the sensitivity of detection of the TCR-like antibodies is decreased on fixed cells.

The possibility to analyze TCR-ligand containing cells within undisturbed tissues might allow, for example, to quantify and localize the HBV infected hepatocytes, to study their co-expression of inhibitory molecules (i.e. PD-1L) in different phases of chronic HBV infection and to detect possible co-localization with CD8 T cells or NK cells.

The two TCR-like antibodies show a different degree of degeneracy of recognition of natural mutants within the two epitopes. The e 183/91 Ab seems exclusively specific for the env 183-91 sequence characteristic of HBV Gen A, C, D, while the single AA substitution at position 187 (Lys to Arg) found in HBV Gen B, E, F isolates completely abolished recognition. These results obtained with peptide pulsed T2 cells were then confirmed by the direct staining of biopsies of CHB patients infected by HBV gen C and D, which were both successfully stained with e183/A2 antibodies. The c18/A2 antibody showed a higher degree of degeneracy, since it was able to recognize many core 18-27 peptides with AA substitutions characteristic of many natural mutations present in the core 18-27 and among them the substitution Ile to Val at position 27. This AA variation altered the binding affinity of the peptide to A201 molecules and thus it reduced the stability of the peptide/A2 complex, making this sequence less immunogenic in A201 subjects and reduced the quantity of pMHC complexes on the surface of infected cells. Such hypothesis was confirmed by the inability of c18/A2 Ab to stain a biopsy of a HBV gen C infected patients despite his quite high level of HBV replication. Since the recognition pattern of the TCR-like antibodies specific for mutation present within the env 183-91/A2 complex is distinct to the one of TCR of env183-91 specific CD8 cells, it is likely that potential mutations within the epitope selected by CD8 T cell pressure wouldn't be able to abolish TCR-like Ab recognition of the selected variant virus.

The strict specificity of the TCR-like mAbs to cells expressing the correct pMHC and the inability of circulating HBV antigens to inhibit the specific binding are results that encourage the use of humanized versions of the TCR-like antibodies described here in therapy and diagnostic. In the new era of personalized medicine, such antibodies could be used to first visualize the existence and quantity of the infected targets and then be directly used to deliver specifically antiviral drugs or cytokines to the viral infected cells.

Example 3

Generation of Anti-E183/A2 TCR-Like Antibodies

Figure 14:
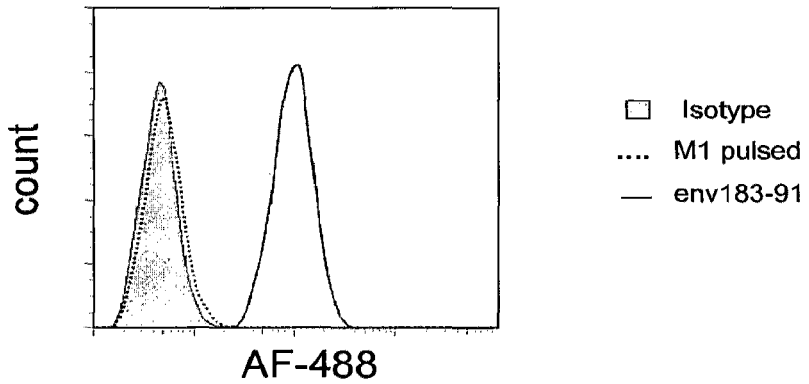
FIG. 14 is a graph of the results of screening of hybridoma supernatant. T2 cells were pulsed with 1 μM each of env183-91 or an irrelevant M1 peptide for 1 hr, washed 3 times and incubated with 50 μl of hybridoma culture supernatant followed by washing and incubation with anti-mouse IgG- AF488 for 30 min. Cells were washed and analyzed on flow cytometry. Culture supernatant specifically stained target cells that are pulsed with env 183-91, but not M1 peptide.

Mice were repeatedly immunized i.p. with a solution containing 25 μg of purified E183/A2 monomer and Freund's complete adjuvant (primary dose) or Freund's incomplete adjuvant (3 booster doses). A final booster dose without adjuvant was performed by tail injection 3 days before fusion. Splenocytes from boosted mice were fused by PEG1500 with NS1 myeloma cells using standard technique. The resulting hybridoma cell mixture was seeded in 96-well plates and selected in HAT medium for 2 weeks. About 2000 hybridomas were screened for the selection of desired mAb specificity by flow cytometry. Either env183-91 peptide pulsed or an irrelevant M1 (flu) peptide pulsed T2 cells were incubated with the hybridoma supernatants for 30 min at 40° C., washed and further incubated with anti-mouse IgG-alexafluor-488 secondary antibodies for 30 min at room temperature, washed and analyzed on BD FACSCAN flow cytometer using cell quest software. Only one clone displayed the required recognition characteristics restricted to env183-HLA-A2 and did not show reactivity with M1 peptide pulsed cells (FIG. 14). This positive clone was sub-cloned twice by limiting dilution, stably expanded and the culture supernatants were collected in bulk. The E183/A2 mAb from these supernatants were purified by Protein G Agarose column.

Specificity of E183/A2 mAb

Figure 15:
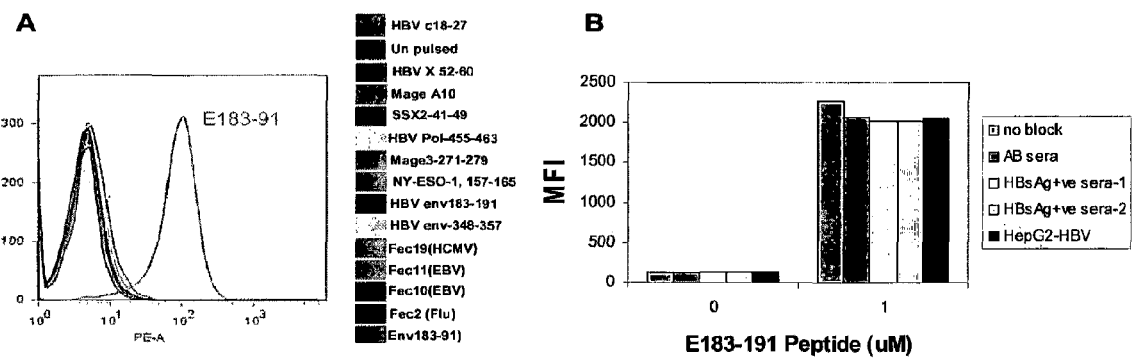
FIG. 15A is a graph of the specificity of E183/A2 mAb. T2 cells were incubated with 1 μM each of listed peptides for 1 hr, washed 3 times and stained with 0.5 μg of mAb. After washing 3 times, cells were incubated with anti-mouse IgG-PE abs for 30 min, washed and acquired on flow cytometer. Specific staining was observed only with env183-91 peptide pulsed cells.
FIG. 15B is a graph showing that the binding capacity of E183/A2 mAb is not inhibited by HBsAg. E183/A2 mAb was pre-incubated with 100 μl of HBsAg+ve sera from two different patients separately, culture supernatants of HBV producing HepG2 cells and with sera of healthy individuals (AB serum). This pre-incubated mAb-sera mixture was used to stain env183-91 pulsed T2 cells. The recognition capacity of E183/A2 mAb was not inhibited by the HBsAg of patient sera.

The specificity of this mAb was tested by incubating T2 cells with different HLA-A2 binding peptides derived from HBV polymerase, X and envelope proteins as well as from EBV, flu, CMV; and a wide variety of tumour associated antigen epitopes. As shown in the FIG. 15A, the E183/A2 mAb reacted specifically with env183-91 peptide pulsed cells and did not stain cells pulsed with any other peptides. Similarly, the mAb did not recognize peptide alone or HLA-A2 alone as pre-incubation of mAb with peptide did not result in the decreased staining of cells pulsed with env183-91 peptide (data not shown). The binding/recognition capacity of therapeutic antibodies should not be inhibited by the components of the patients' sera as well as viral antigens. To determine if E183/A2 mAb retains its binding capacity even in the presence of patient's sera components including high levels of HBsAg and free virions, the mAb was pre-incubated with sera of HBsAg+ve patients, culture supernatants from HBV producing HepG2 cells and with the sera of healthy individuals (AB serum). The resulting mixture was then used to stain env183-91 pulsed T2 cells. FIG. 15B demonstrates that pre-incubation of mAb with HBeAg+ve sera have no inhibitory effect on the recognition of E183/A2 complexes by E183/A2 mAb. Taken together, these results clearly demonstrate that peptide specific and MHC-restricted E183/A2 mAb exhibited a fine specificity of a T Cell Receptor and its binding capacity is not perturbed by HBsAg.

Sensitivity of E183/A2 mAb

Figure 16:
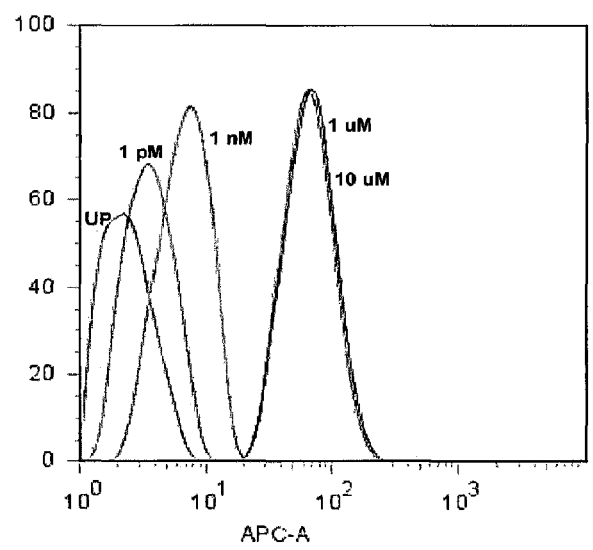
FIG. 16 is a graph showing the minimal concentration of env183-91 peptide needed for detection by E183/A2 mAb. T2 cells were pulsed for 1 hr with titrated amounts of env183-91 peptide and stained with TCR-like mAb. As low as pM peptide is sufficient to achieve significant staining.

To find out the minimal peptide concentration required to achieve significant staining with E183/A2 mAb, T2 cells were incubated with various concentration of env183-91 peptide and stained with mAb. As shown in the FIG. 16, as low as 1 pM peptide is sufficient to achieve the significant staining.

Mapping of Antibody Binding Sites on env 183-191 Peptide

Figure 17:
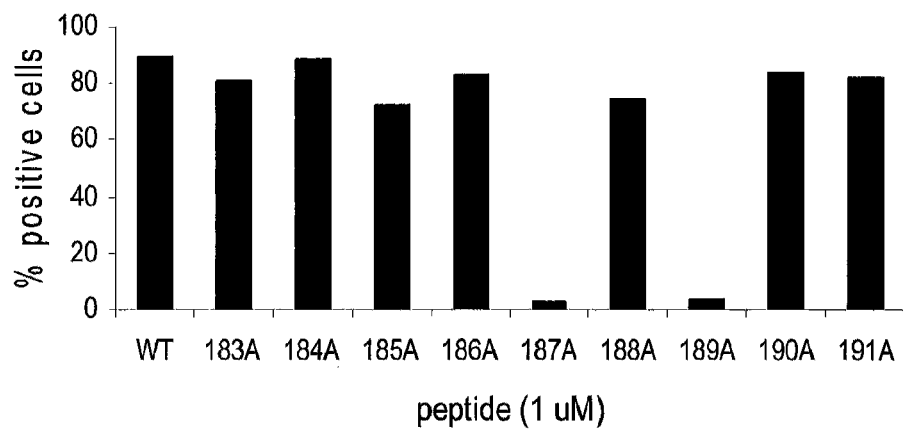
FIG. 17 is a graph showing peptide mapping. T2 cells were pulsed with 1 μM peptide as indicated and cells were incubated with E183/A2 mAb for 1 hr. The binding of E183/A2 antibody was detected by flow cytometric analysis. Amino acids 186 and 188 are the residues with which antibody recognizes the complex.

To address which amino acid residues of env183-91 peptide are directly involved for E183/A2 mAb recognition, T2 cells were incubated with env183-191 peptide carrying alanine substitutions at the indicated residues and the ability of E183/A2 mAb to recognize the AA substituted peptides was tested. FIG. 17 showed that AA substitutions at position 187 and 189 were not tolerated by E183/A2 mAb, indicating the involvement of these residues in antibody recognition.

Recognition of E183/A2 Complexes Formed by Intracellular Processing

The capacity of TCR-like mAb to recognize pMHC complexes produced by physiologically active intracellularly processed peptide in the context of HLA-A2 was first evaluated by flow cytometry analysis. For this purpose, lentiviral-mediated transduction of HepG2 cells (which are HLA-A201+) with pLVX-HBsAg vector expressing full length HBsAg protein. Significant staining with E183/A2 mAb above empty vector transduced cells could be clearly seen (FIG. 18A), demonstrating that these antibodies can recognize pMHC complexes produced endogenously in hepatocytes.

Figure 18:
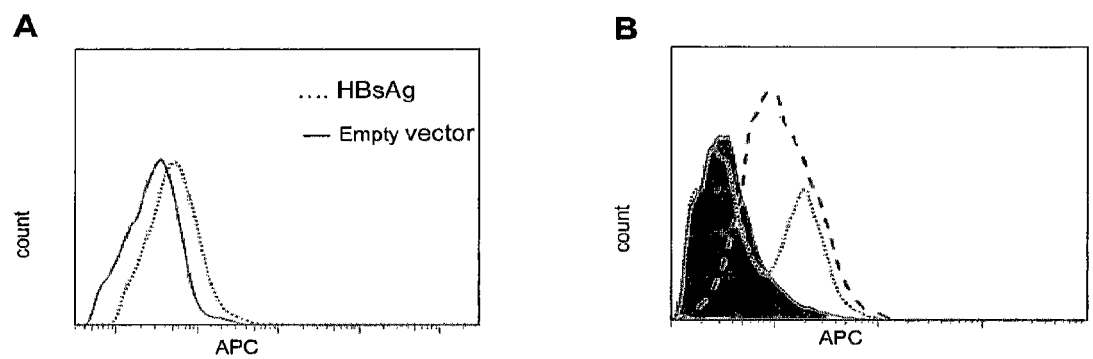
FIG. 18 is a graph showing the recognition of pMHC complexes produced by intracellular processing. HepG2 cells were transduced with HBsAg (A) lentiviral vectors. Empty vector transduced cells were used as control. Cells were incubated with E183/A2 antibody followed by incubation with goat anti-mouse IgG-APC and analyzed by flow cytometry. Significant staining above the empty vector transduced cells is clearly seen. (B) HBV producing HepG2-117 cells were grown in the presence or absence of Doxocycline and IFN-γ and stained with E183/A2 mAb as indicated above. Significant staining above the empty vector control cells was clearly seen in both cases.

The ability of TCR like antibody to recognize pMHC complexes on HBV producing HepG2 (HepG2-117) cells was then tested. These cells were stably transfected with whole HBV genome and produce HBV upon removal of doxocycline from the culture medium. Six days after removal of Dox from HepG2-117 cells, about 40% cells were stained with E183/A2 mAb (FIG. 18B). To increase HBV and MHC-class I expression, HepG2-117 cells were treated with DMSO, and IFN-γ, and significantly increased staining with E183/A2 antibody was observed, demonstrating the ability of the TCR-like antibody to recognize their cognate pMHC on HBV producing cells. Taken together these results indicate that the TCR-like E183/A2 mAb is capable of detecting specific complexes formed after active and naturally occurring endogenous intracellular processing.

Detection of E183/A2 Complexes by Immunocytochemistry

Figure 19:
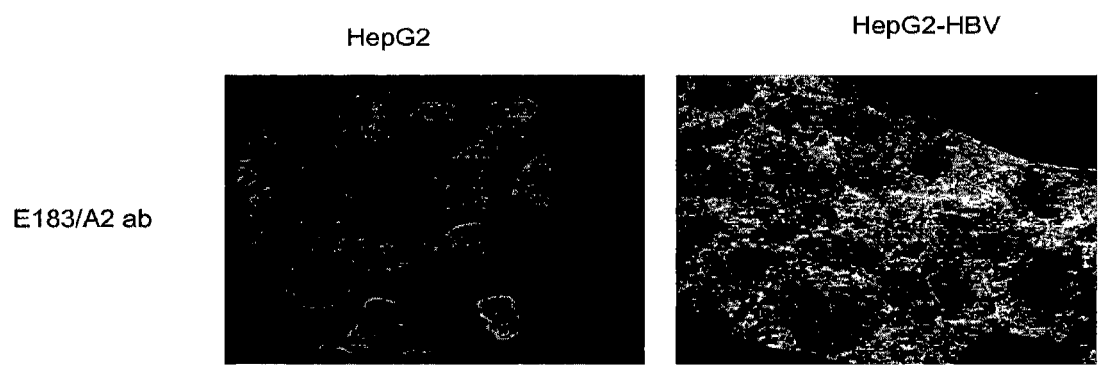
FIG. 19 are photographs of immunocytochemical staining of E183/A2 complexes. HBV expressing HepG2 cells (HepG2-117) and vector control HepG2 cells were treated with DMSO and IFN-γ and fixed with 1% PFA, and stained with E183/A2 mAb. Tyramide Signal Amplification kit was used to detect the binding. Nuclei were stained with DAPI (Blue, shown as light grey in FIG. 19). The E183/A2 mAb is able to visualize E183/A2 complexes (Red, shown as dark grey in FIG. 19) that are presented by natural intracellular processing of HBsAg in HBV producing cells.

Another major potential application of TCR-like antibody is the direct in situ visualization of ligand containing cells within undisturbed tissues using Immunocytochemical methods. As a first step to assess this potential we determined whether the E183/A2 mAb can be used for such studies by testing its ability to detect E183/A2 complexes on HBV-producing HepG2 cells (HepG2-117). Cells as treated in FIG. 18B were fixed in 1% paraformaldehyde for 15 min at room temperature, washed and incubated with E183/A2 mAb. Following washing thrice, the Alexa fluor647-Tyramide Signal Amplification kit was used for visualization of staining with the exception that anti-mouse IgG-HRP polymer was used in place of anti-mouse IgG-HRP. As shown in FIG. 19, significant staining could be observed with E183/A2 mAb and no staining was observed HepG2 cells that are not producing HBV. These results demonstrate that E183/A2 mAb could be used to visualize the E183/A2 complexes on fixed infected cells.

Detection of E183/A2 Complexes on HCC Lines

Figure 20:
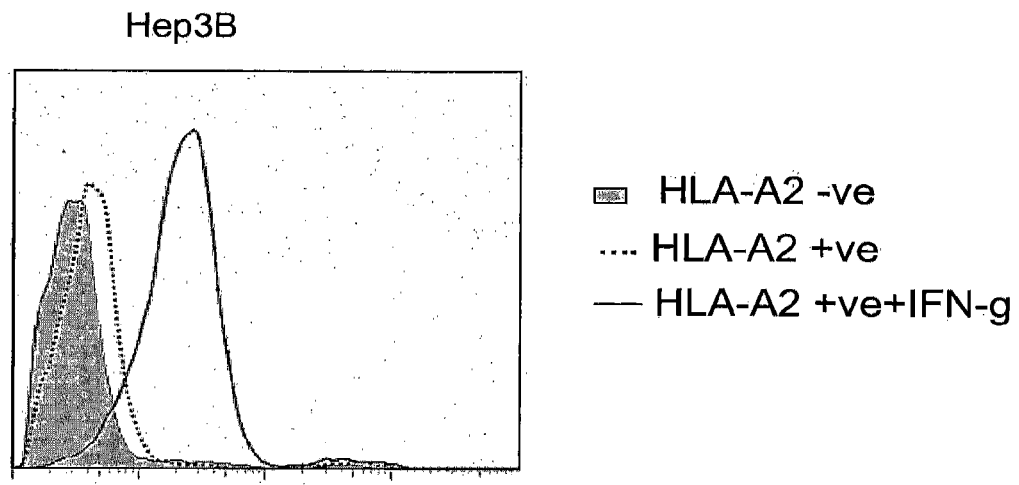
FIG. 20 is a graph showing the ability of E183/A2 mAb to recognize HCC cells with natural HBV integration. Hep3B (a natural HCC cell line expressing HBV envelope antigen) was transduced with HLA-A2 expressing vector (Hep3B-A2). Cells were treated with and without 1000 IU/ml IFN-γ for 2 days and stained with E183/A2 mAb as described earlier and cells were analyzed on flow cytometer.

To explore the potential of the E183/A2 TCR like mAb to recognizing the endogenously derived pMHC complexes produced on HCC lines that have naturally integrated HBV DNA, a well characterized patient derived cell line, Hep3B was used. This HCC cell line was previously shown to express and elaborate HBsAg with out artificial ectopic transfections and they simulate the cells of the diseased hepatocytes in patients where the pMHC complexes are expected to be present at low density on the cell surface compared to the peptide-loaded cells. Because this cell line does not express HLA-A2, we transduced cells with HLA-A2 vector. Flow cytometry analysis revealed significant staining following incubation with E183/A2 mAb. No staining was observed with cells that do not express HLA-A2 (FIG. 20). Treatment of these cells with IFNg increased the antibody staining significantly. This data indicated that the E183/A2 antibody can recognize pMHC on natural HCC lines and therefore may eventually be used to visualize these complexes on the surface of HCC lines that express HBsAg naturally.

Specific Delivery of Fluorochrome Linked to E183/A2 mAb

Figure 21:
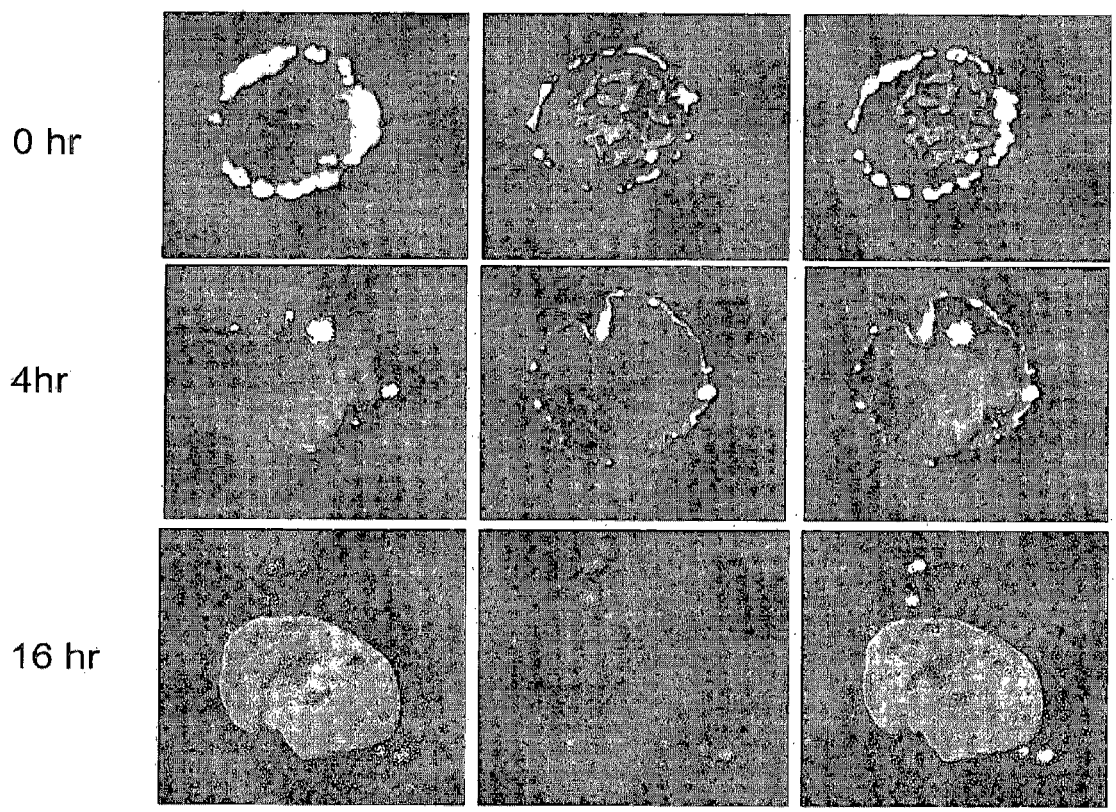
FIG. 21 are photographs showing targeted delivery of immuno-fluorochrome. HepG2 cells were pulsed with E183-91 peptide and incubated with antibody-fluorochrome conjugate for 1 hr, washed and incubated at 37° C. on cover slips. At different time points after incubation, cover slips were collected and incubated with Dil red (shown as a medium grey in FIG. 21) to label plasma membrane or LysoTracker dye to trace lysosomes in the cells. Cell nuclei were stained with DAPI (Blue, shown as dark grey in FIG. 21). Cells on cover slips were fixed with 1% PFA and mounted for confocal imaging. E183/A2 mAb-fluorochrome is shown by Green/bright grey in FIG. 21.

To demonstrate the ability of the antibody to serve as a specific targeting molecule, a fluorochrome-Fab (Alexa Fluor 488, Zenon labeling) was conjugated to the E183/A2 antibody and tested if the immuno-fluorochrome conjugate is specifically delivered to the pMHC expressing cells. The flow cytometry analysis revealed that the mAb-fluorochrome conjugate retained its parental antibody specificity as specific binding was observed with E183-91 peptide loaded cells but not to, the cells loaded with an irrelevant peptide (data not shown). Following incubation of E183-91 peptide loaded HepG2 cells with the mAb-fluorochrome conjugate, the cells were incubated at 37° C. At fixed time points an aliquots of cells were collected and incubated with Dil Red to label plasma membrane to visualize the internalization of conjugate. On confocal imaging, cells at 0 hr showed a ring-like distribution of cell surface fluorescence along with plasma membrane-specific dye Dil red. By 4 hr of incubation, majority of surface fluorescence was delivered to cell and appeared with in the cell as small speckles. To be an effective drug delivery vehicle antibody should not only internalize into target cells but should follow intracellular route ending with the delivery of the drug to the correct intracellular address. Aliquots of these cells at 16 hr were incubated with LysoTracker red (shown as medium grey in FIG. 21) to determine whether the internalized antibody costained with lysosomes. Analysis of the results as shown in FIG. 21 confirms the co-localization of mAb-fluorochrome and lysosomes (shown as bright grey in FIG. 21). Taken together these results clearly indicated that mAb is able to deliver the cargo attached to it into hepatocytes expressing pMHC.

REFERENCES

Gehring A. J et al. (2007). The Level of Viral Antigen Presented by Hepatocytes Influences CD8 T-Cell Function. J Virol.; 81(6): 2940-2949.
Morrison, et al., 1984, Proc. Natl. Acad. Sci., 81, 6851-6855;
Sambrook and Russel, Molecular Cloning: A Laboratory Manual, Cold Springs Harbor Laboratory, New York (2001);
Sun D, Nassal M. (2006) Stable HepG2- and Huh-based human hepatoma cell lines for efficient regulated expression of infectious Hepatitis B virus. Journal of Hepatology 45:636-645.
U.S. Pat. No. 5,225,539;
U.S. Pat. No. 5,585,089;

The invention claimed is:

1. An isolated TCR-like antibody or fragment thereof, wherein the antibody or fragment thereof is specifically binding to at least one HBV derived peptide, wherein the HBV derived peptide comprises HBe183-191 of SEQ ID NO: 24 and is part of a HLA-A2 peptide complex, the complex comprising the HBV derived peptide and a HLA-A2 molecule, wherein the antibody is selected form the group consisting of:
   a) an antibody produced by hybridoma cell line deposited with ATCC with accession number PTA-11068 and
   b) an antibody comprising at least one light chain and at least one heavy chain, wherein the light chain comprises the amino acid sequence of SEQ ID NO: 32, and the heavy chain comprises the amino acid sequence of SEQ ID NO: 33, wherein the antibody is capable of distinguishing HBV-infected cells from uninfected cells.

2. An isolated TCR-like antibody or fragment thereof, wherein the antibody or fragment thereof is specifically binding to at least one HBV derived peptide, wherein the HBV derived peptide comprises HBc 18-27 of SEQ ID NO: 3 and is part of a HLA-A2 peptide complex, the complex comprising the HBV derived peptide and a HLA-A2 molecule, wherein the antibody is selected from the group consisting of:
   (a) an antibody produced by hybridoma cell line deposited with ATCC with accession number PTA-10167;
   (b) an antibody comprising at least one light chain and at least one heavy chain, wherein the light chain comprises the amino acid sequence of SEQ ID NO: 1, and the heavy chain comprises the amino acid sequence of SEQ ID NO: 2, wherein the antibody is capable of distinguishing HBV-infected cells from uninfected cells.

3. An isolated hybridoma cell line deposited with the ATCC selected from the group consisting of cell line with accession number PTA-10167 and cell line with accession number PTA-11068.

* * * * *

SEQUENCE LISTING

```
<160> NUMBER OF SEQ ID NOS: 34

<210> SEQ ID NO 1
<211> LENGTH: 107
<212> TYPE: PRT
<213> ORGANISM: unknown
<220> FEATURE:
<223> OTHER INFORMATION: murinae
<220> FEATURE:
<221> NAME/KEY: misc_feature
<223> OTHER INFORMATION: Amino acid sequence of variable domain of
      c18/A2 mAb Light Chain
<220> FEATURE:
<221> NAME/KEY: misc_feature
<223> OTHER INFORMATION: Amino acid sequence of variable domain of
      c18/A2mAb Light Chain

<400> SEQUENCE: 1

Asp Ile Gln Met Thr Gln Ser Pro Ala Ser Leu Ser Thr Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Trp Ser Thr Pro Phe
                85                  90                  95

Thr Phe Gly Ser Gly Thr Lys Leu Glu Ile Lys
            100                 105

<210> SEQ ID NO 2
<211> LENGTH: 120
<212> TYPE: PRT
<213> ORGANISM: unknown
<220> FEATURE:
```

```
<223> OTHER INFORMATION: Murinae
<220> FEATURE:
<221> NAME/KEY: misc_feature
<223> OTHER INFORMATION: Amino acid sequence of variable domain of
      c18/A2 mAb Heavy Chain
<220> FEATURE:
<221> NAME/KEY: misc_feature
<223> OTHER INFORMATION: Amino acid sequence of variable domain of
      c18/A2mAb Heavy Chain

<400> SEQUENCE: 2

Gln Val Gln Leu Gln Gln Ser Gly Pro Glu Leu Val Lys Pro Gly Ala
1               5                   10                  15

Ser Val Lys Ile Ser Cys Lys Ala Ser Gly His Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asn Ser Ala Val Tyr Phe Cys
                85                  90                  95

Ala Arg Arg Asp Tyr Gly Tyr Ser Tyr Ala Met Asp Tyr Trp Gly Gln
            100                 105                 110

Gly Thr Ser Val Thr Val Ser Ser
        115                 120

<210> SEQ ID NO 3
<211> LENGTH: 10
<212> TYPE: PRT
<213> ORGANISM: Hepatitis B virus
<220> FEATURE:
<221> NAME/KEY: misc_feature
<223> OTHER INFORMATION: HBc18-27 peptide
<220> FEATURE:
<221> NAME/KEY: misc_feature
<223> OTHER INFORMATION: HBc18-27 peptide (HBV genotype A/D/E/F)

<400> SEQUENCE: 3

Phe Leu Pro Ser Asp Phe Phe Pro Ser Val
1               5                   10

<210> SEQ ID NO 4
<211> LENGTH: 10
<212> TYPE: PRT
<213> ORGANISM: Hepatitis B virus
<220> FEATURE:
<221> NAME/KEY: misc_feature
<223> OTHER INFORMATION: HBc18-27 peptide (HBV genotype B/C)

<400> SEQUENCE: 4

Phe Leu Pro Ser Asp Phe Phe Pro Ser Ile
1               5                   10

<210> SEQ ID NO 5
<211> LENGTH: 10
<212> TYPE: PRT
<213> ORGANISM: Hepatitis B virus
<220> FEATURE:
<221> NAME/KEY: misc_feature
<223> OTHER INFORMATION: A21

<400> SEQUENCE: 5

Phe Leu Pro Ala Asp Phe Phe Pro Ser Val
```

```
1               5                  10
```

<210> SEQ ID NO 6
<211> LENGTH: 10
<212> TYPE: PRT
<213> ORGANISM: Hepatitis B virus
<220> FEATURE:
<221> NAME/KEY: misc_feature
<223> OTHER INFORMATION: Y23

<400> SEQUENCE: 6

```
Phe Leu Pro Ser Asp Tyr Phe Pro Ser Val
1               5                  10
```

<210> SEQ ID NO 7
<211> LENGTH: 10
<212> TYPE: PRT
<213> ORGANISM: Hepatitis B virus
<220> FEATURE:
<221> NAME/KEY: misc_feature
<223> OTHER INFORMATION: Y24

<400> SEQUENCE: 7

```
Phe Leu Pro Ser Asp Phe Tyr Pro Ser Val
1               5                  10
```

<210> SEQ ID NO 8
<211> LENGTH: 10
<212> TYPE: PRT
<213> ORGANISM: Hepatitis B virus
<220> FEATURE:
<221> NAME/KEY: misc_feature
<223> OTHER INFORMATION: Asn21-A27

<400> SEQUENCE: 8

```
Phe Leu Pro Asn Asp Phe Phe Pro Ser Ala
1               5                  10
```

<210> SEQ ID NO 9
<211> LENGTH: 10
<212> TYPE: PRT
<213> ORGANISM: Hepatitis B virus
<220> FEATURE:
<221> NAME/KEY: misc_feature
<223> OTHER INFORMATION: Asn21

<400> SEQUENCE: 9

```
Phe Leu Pro Asn Asp Phe Phe Pro Ser Val
1               5                  10
```

<210> SEQ ID NO 10
<211> LENGTH: 10
<212> TYPE: PRT
<213> ORGANISM: Hepatitis B virus
<220> FEATURE:
<221> NAME/KEY: misc_feature
<223> OTHER INFORMATION: A27

<400> SEQUENCE: 10

```
Phe Leu Pro Ser Asp Phe Phe Pro Ser Ala
1               5                  10
```

<210> SEQ ID NO 11
<211> LENGTH: 10
<212> TYPE: PRT
<213> ORGANISM: Hepatitis B virus
<220> FEATURE:
<221> NAME/KEY: misc_feature

<223> OTHER INFORMATION: P21

<400> SEQUENCE: 11

Phe Leu Pro Pro Asp Phe Phe Pro Ser Val
1               5                   10

<210> SEQ ID NO 12
<211> LENGTH: 10
<212> TYPE: PRT
<213> ORGANISM: Hepatitis B virus
<220> FEATURE:
<221> NAME/KEY: misc_feature
<223> OTHER INFORMATION: P21

<400> SEQUENCE: 12

Phe Leu Pro Ser Asp Phe Leu Pro Ser Val
1               5                   10

<210> SEQ ID NO 13
<211> LENGTH: 10
<212> TYPE: PRT
<213> ORGANISM: Hepatitis B virus
<220> FEATURE:
<221> NAME/KEY: misc_feature
<223> OTHER INFORMATION: 26G

<400> SEQUENCE: 13

Phe Leu Pro Ser Asp Phe Phe Pro Gly Val
1               5                   10

<210> SEQ ID NO 14
<211> LENGTH: 10
<212> TYPE: PRT
<213> ORGANISM: Hepatitis B virus
<220> FEATURE:
<221> NAME/KEY: misc_feature
<223> OTHER INFORMATION: A21-I27

<400> SEQUENCE: 14

Phe Leu Pro Ala Asp Phe Phe Pro Ser Ile
1               5                   10

<210> SEQ ID NO 15
<211> LENGTH: 10
<212> TYPE: PRT
<213> ORGANISM: Hepatitis B virus
<220> FEATURE:
<221> NAME/KEY: misc_feature
<223> OTHER INFORMATION: E22

<400> SEQUENCE: 15

Phe Leu Pro Ser Glu Phe Phe Pro Ser Val
1               5                   10

<210> SEQ ID NO 16
<211> LENGTH: 10
<212> TYPE: PRT
<213> ORGANISM: Hepatitis B virus
<220> FEATURE:
<221> NAME/KEY: misc_feature
<223> OTHER INFORMATION: 22*91

<400> SEQUENCE: 16

Phe Leu Pro Ser Asp Thr Asn Met Gly Leu
1               5                   10

<210> SEQ ID NO 17

```
<211> LENGTH: 9
<212> TYPE: PRT
<213> ORGANISM: Influenza virus
<220> FEATURE:
<221> NAME/KEY: misc_feature
<223> OTHER INFORMATION: M1 peptide/ FEC1 (Flu)

<400> SEQUENCE: 17

Gly Ile Leu Gly Phe Val Phe Thr Leu
1               5

<210> SEQ ID NO 18
<211> LENGTH: 9
<212> TYPE: PRT
<213> ORGANISM: Hepatitis B virus
<220> FEATURE:
<221> NAME/KEY: Misc_feature
<223> OTHER INFORMATION: HBV X, 52-60

<400> SEQUENCE: 18

His Leu Ser Leu Arg Gly Leu Pro Val
1               5

<210> SEQ ID NO 19
<211> LENGTH: 9
<212> TYPE: PRT
<213> ORGANISM: Homo sapiens
<220> FEATURE:
<221> NAME/KEY: Misc_feature
<223> OTHER INFORMATION: Mage A10, 254-262

<400> SEQUENCE: 19

Gly Leu Tyr Asp Gly Met Glu His Leu
1               5

<210> SEQ ID NO 20
<211> LENGTH: 9
<212> TYPE: PRT
<213> ORGANISM: Homo sapiens
<220> FEATURE:
<221> NAME/KEY: Misc_feature
<223> OTHER INFORMATION: SSX2, 41-49

<400> SEQUENCE: 20

Lys Ala Ser Glu Lys Ile Phe Tyr Val
1               5

<210> SEQ ID NO 21
<211> LENGTH: 9
<212> TYPE: PRT
<213> ORGANISM: Hepatitis B virus
<220> FEATURE:
<221> NAME/KEY: Misc_feature
<223> OTHER INFORMATION: HBV pol, 455-463

<400> SEQUENCE: 21

Gly Leu Ser Arg Tyr Val Ala Arg Leu
1               5

<210> SEQ ID NO 22
<211> LENGTH: 9
<212> TYPE: PRT
<213> ORGANISM: Homo sapiens
<220> FEATURE:
<221> NAME/KEY: Misc_feature
<223> OTHER INFORMATION: Mage3, 271-279

<400> SEQUENCE: 22
```

```
Phe Leu Trp Gly Pro Arg Ala Leu Val
1               5

<210> SEQ ID NO 23
<211> LENGTH: 9
<212> TYPE: PRT
<213> ORGANISM: Homo sapiens
<220> FEATURE:
<221> NAME/KEY: Misc_feature
<223> OTHER INFORMATION: NY-ESO-1, 157-165

<400> SEQUENCE: 23

Ser Leu Leu Met Trp Ile Thr Gln Ala
1               5

<210> SEQ ID NO 24
<211> LENGTH: 9
<212> TYPE: PRT
<213> ORGANISM: Hepatitis B virus
<220> FEATURE:
<221> NAME/KEY: Misc_feature
<223> OTHER INFORMATION: HBV env, 183-191

<400> SEQUENCE: 24

Phe Leu Leu Thr Arg Ile Leu Thr Ile
1               5

<210> SEQ ID NO 25
<211> LENGTH: 10
<212> TYPE: PRT
<213> ORGANISM: Hepatitis B virus
<220> FEATURE:
<221> NAME/KEY: Misc_feature
<223> OTHER INFORMATION: HBV env, 348-357

<400> SEQUENCE: 25

Gly Leu Ser Pro Thr Val Trp Leu Ser Val
1               5                   10

<210> SEQ ID NO 26
<211> LENGTH: 9
<212> TYPE: PRT
<213> ORGANISM: Human cytomegalovirus
<220> FEATURE:
<221> NAME/KEY: Misc_feature
<223> OTHER INFORMATION: FEC19 (HCMV)

<400> SEQUENCE: 26

Asn Leu Val Pro Met Val Ala Thr Val
1               5

<210> SEQ ID NO 27
<211> LENGTH: 9
<212> TYPE: PRT
<213> ORGANISM: unknown
<220> FEATURE:
<223> OTHER INFORMATION: Epstein-Barr Virus
<220> FEATURE:
<221> NAME/KEY: Misc_Feature
<223> OTHER INFORMATION: FEC11 (EBV)

<400> SEQUENCE: 27

Gly Leu Cys Thr Leu Val Ala Met Leu
1               5

<210> SEQ ID NO 28
<211> LENGTH: 9
<212> TYPE: PRT
```

<210> SEQ ID NO 28
<211> LENGTH: 8
<212> TYPE: PRT
<213> ORGANISM: unknown
<220> FEATURE:
<223> OTHER INFORMATION: Epstein-Barr Virus
<220> FEATURE:
<221> NAME/KEY: Misc_feature
<223> OTHER INFORMATION: FEC10 (EBV)

<400> SEQUENCE: 28

Cys Leu Gly Gly Leu Leu Thr Met Val
1               5

<210> SEQ ID NO 29
<211> LENGTH: 9
<212> TYPE: PRT
<213> ORGANISM: Influenza virus
<220> FEATURE:
<221> NAME/KEY: Misc_feature
<223> OTHER INFORMATION: FEC2 (Flu)

<400> SEQUENCE: 29

Phe Met Tyr Ser Asp Phe His Phe Ile
1               5

<210> SEQ ID NO 30
<211> LENGTH: 321
<212> TYPE: DNA
<213> ORGANISM: unknown
<220> FEATURE:
<223> OTHER INFORMATION: Murinae
<220> FEATURE:
<221> NAME/KEY: misc_feature
<223> OTHER INFORMATION: Nucleotide sequence of variable domain of
    c18/A2 mAb Light Chain
<220> FEATURE:
<221> NAME/KEY: misc_feature
<223> OTHER INFORMATION: Nucleotide seq of variable domain of
    c18/A2mAb Light Chain

<400> SEQUENCE: 30
gacatccaga tgactcagtc tccagcctcc ctatctacat ctgtgggaga aactgtcacc      60
atcacatgtc gagcaagtgg gaatattcac aattatttag catggtatca gcagaaacag     120
ggaaaatctc ctcagctcct ggtctataat gcaaaaacct tagcagatgg tgtgccatca     180
aggttcagtg gcagtggatc aggaacacaa ttttctctca agatcaacag cctgcagcct     240
gaagattttg ggagttatta ctgtcaacat ttttggagta ctccattcac gttcggctcg     300
gggacaaagt tggaaataaa a                                                321

<210> SEQ ID NO 31
<211> LENGTH: 360
<212> TYPE: DNA
<213> ORGANISM: unknown
<220> FEATURE:
<223> OTHER INFORMATION: murinae
<220> FEATURE:
<221> NAME/KEY: misc_feature
<223> OTHER INFORMATION: Nucleotide sequence of variable domain of
    c18/A2 mAb Heavy Chain
<220> FEATURE:
<221> NAME/KEY: misc_feature
<223> OTHER INFORMATION: Nucleotide seq of variable domain of
    c18/A2mAb Heavy Chain

<400> SEQUENCE: 31
caggttcagc tgcagcagtc tggacctgag ctggtgaagc ctggggcttc agtgaagata      60
tcctgcaagg cttctggtca caccttcaca agctacgata taaactgggt gaagcagagg     120
cctggacagg gacttgagtg gattggatgg atttatcctg agatggaag tactaagtac      180

-continued

```
aatgagaaat tcaagggcaa ggccacactg actgcagaca atcctccag cacagcctac      240 atgcagctca gcagcctgac ttctgagaac tctgcagtct atttctgtgc aagaagggac     300
tacggctact cttatgctat ggactactgg ggtcaaggaa cctcagtcac cgtctcctca     360
```

<210> SEQ ID NO 32
<211> LENGTH: 108
<212> TYPE: PRT
<213> ORGANISM: unknown
<220> FEATURE:
<223> OTHER INFORMATION: murinae
<220> FEATURE:
<221> NAME/KEY: Misc_feature
<223> OTHER INFORMATION: Amino acid sequence of variable domain of
      e183/A2 mAb Light Chain
<220> FEATURE:
<221> NAME/KEY: Misc_feature
<223> OTHER INFORMATION: a.a. seq of variable domain of e183/A2mAb
      Light Chain

<400> SEQUENCE: 32

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr His Gln Lys Gln Gly Lys Ser Pro Gln Leu Leu Val
        35                  40                  45

Tyr Ile Ala Lys Thr Leu Ala Glu Gly Val Pro Ser Arg Phe Ser Gly
    50                  55                  60

Ser Gly Ser Gly Thr Gln Phe Ser Leu Lys Ile Asp Ser Leu Gln Pro
65                  70                  75                  80

Glu Asp Val Gly Ser Tyr Tyr Cys Gln His His Tyr Gly Thr Pro Tyr
                85                  90                  95

Thr Phe Gly Gly Gly Thr Lys Leu Glu Ile Lys Arg
            100                 105

<210> SEQ ID NO 33
<211> LENGTH: 107
<212> TYPE: PRT
<213> ORGANISM: unknown
<220> FEATURE:
<223> OTHER INFORMATION: murinae
<220> FEATURE:
<221> NAME/KEY: Misc_feature
<223> OTHER INFORMATION: Amino acid sequence of variable domain of
      e183/A2 mAb Heavy Chain
<220> FEATURE:
<221> NAME/KEY: Misc_feature
<223> OTHER INFORMATION: a.a seq of variable domain of e183/A2mAb
      Heavy Chain

<400> SEQUENCE: 33

Gln Val Gln Leu Gln Gln Pro Gly Ala Glu Phe Val Lys Pro Gly Ala
1               5                   10                  15

Ser Val Arg Leu Ser Cys Lys Ala Ser Gly Tyr Thr Phe Ser Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

```
Met Gln Phe Ser Ser Leu Thr Ser Glu Asp Ser Ala Val Tyr Tyr Cys
                85                  90                  95

Ala Thr Ser Gly Tyr Asp Val Gly Val Asp Tyr
            100                 105

<210> SEQ ID NO 34
<211> LENGTH: 9
<212> TYPE: PRT
<213> ORGANISM: Hepatitis B virus
<220> FEATURE:
<221> NAME/KEY: Misc_feature
<223> OTHER INFORMATION: HBC 19-27I peptide

<400> SEQUENCE: 34

Leu Pro Ser Asp Phe Phe Pro Ser Ile
1               5
```